US010940325B2

(12) United States Patent
Grinberg et al.

(10) Patent No.: US 10,940,325 B2
(45) Date of Patent: *Mar. 9, 2021

(54) ASYSTOLE DETECTION AND RESPONSE IN AN IMPLANTABLE CARDIOVERTER DEFIBRILLATOR

(71) Applicant: Medtronic, Inc., Minneapolis, MN (US)

(72) Inventors: Yanina Grinberg, Plymouth, MN (US); Robert T. Sawchuk, Roseville, MN (US); Amy E. Thompson-Nauman, Ham Lake, MN (US); Douglas A. Peterson, Apple Valley, MN (US); Paul R. Solheim, Blaine, MN (US); Joel R. Lauer, Clearwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 34 days.

This patent is subject to a terminal disclaimer.

(21) Appl. No.: 16/195,015

(22) Filed: Nov. 19, 2018

(65) Prior Publication Data

US 2019/0083804 A1 Mar. 21, 2019

Related U.S. Application Data

(63) Continuation of application No. 15/142,074, filed on Apr. 29, 2016, now Pat. No. 10,130,824.
(Continued)

(51) Int. Cl.
*A61N 1/39* (2006.01)
*A61N 1/37* (2006.01)
(Continued)

(52) U.S. Cl.
CPC ......... *A61N 1/3987* (2013.01); *A61N 1/3621* (2013.01); *A61N 1/371* (2013.01);
(Continued)

(58) Field of Classification Search
CPC .... A61N 1/3987; A61N 1/3621; A61N 1/371; A61N 1/37217; A61N 1/37258; A61N 1/3956
See application file for complete search history.

(56) References Cited

U.S. PATENT DOCUMENTS 4,485,813 A 12/1984 Anderson et al.
5,052,388 A 10/1991 Sivula et al.
(Continued)

FOREIGN PATENT DOCUMENTS

WO 2007075732 A2 7/2007

OTHER PUBLICATIONS

Tanaka et al., "Ventricular Asystole Due to Atrial Oversensing by a VVI Pacemaker: VVT Mode as a Simple Solution", Journal of Arrhythmia, vol. 28, 2012, 3 pages.
(Continued)

*Primary Examiner* — William J Levicky

(57) ABSTRACT

An implantable cardioverter defibrillator (ICD) receives a cardiac electrical signal by a sensing circuit while operating in a sensing without pacing mode and detects asystole based on the cardiac electrical signal. The ICD determines, in response to detecting the asystole, if asystole backup pacing is enabled, and automatically switches to a temporary pacing mode in response to the asystole backup pacing being enabled. Other examples of detecting asystole and providing a response to detecting asystole by the ICD are described herein.

22 Claims, 13 Drawing Sheets

FIG. 1A

Related U.S. Application Data

(60) Provisional application No. 62/328,803, filed on Apr. 28, 2016.

(51) Int. Cl.
*A61N 1/362* (2006.01)
*A61N 1/372* (2006.01)

(52) U.S. Cl.
CPC ..... *A61N 1/37217* (2013.01); *A61N 1/37258* (2013.01); *A61N 1/3925* (2013.01); *A61N 1/3956* (2013.01); *A61N 1/3962* (2013.01)

(56) References Cited

U.S. PATENT DOCUMENTS

| | | |
|---|---|---|
| 5,074,301 A | 12/1991 | Gill |
| 5,156,148 A * | 10/1992 | Cohen ................ A61N 1/36564 607/14 |
| 5,545,186 A | 8/1996 | Olson et al. |
| 5,562,711 A | 10/1996 | Yerich et al. |
| 5,593,431 A | 1/1997 | Sheldon |
| 5,766,225 A | 6/1998 | Kramm |
| 6,066,743 A | 5/2000 | Nick et al. |
| 6,253,108 B1 | 6/2001 | Rosborough et al. |
| 6,259,949 B1 | 7/2001 | Rosborough et al. |
| 6,263,241 B1 | 7/2001 | Rosborough et al. |
| 6,298,267 B1 | 10/2001 | Rosborough et al. |
| 6,304,773 B1 | 10/2001 | Taylor et al. |
| 6,449,508 B1 | 9/2002 | Sheldon et al. |
| 6,477,415 B1 * | 11/2002 | Yerich ................ A61N 1/3622 607/25 |
| 6,556,865 B2 | 4/2003 | Walcott et al. |
| 6,760,621 B2 | 7/2004 | Walcott et al. |
| 7,031,772 B2 | 4/2006 | Condie et al. |
| 7,277,752 B2 * | 10/2007 | Matos ................ A61N 1/0492 607/5 |
| 7,392,081 B2 * | 6/2008 | Wagner ................ A61N 1/3962 607/4 |
| 7,570,997 B2 | 8/2009 | Lovett et al. |
| 7,761,150 B2 | 7/2010 | Ghanem et al. |
| 7,979,122 B2 | 7/2011 | Favet et al. |
| 8,578,118 B2 | 11/2013 | Kleckner et al. |
| 8,694,097 B2 | 4/2014 | Cao et al. |
| 8,831,713 B2 | 9/2014 | Stadler et al. |
| 8,886,296 B2 | 11/2014 | Patel |
| 9,144,683 B2 | 9/2015 | Bardy et al. |
| 9,168,380 B1 | 10/2015 | Greenhut et al. |
| 9,278,229 B1 | 3/2016 | Reinke et al. |
| 9,956,423 B2 | 5/2018 | Zhang et al. |
| 10,080,891 B2 | 9/2018 | Thompson-Nauman et al. |
| 2003/0130697 A1 | 7/2003 | Halperin et al. |
| 2004/0172066 A1 | 9/2004 | Wagner et al. |
| 2004/0215239 A1 | 10/2004 | Favet et al. |
| 2007/0203524 A1 | 8/2007 | Sheldon et al. |
| 2010/0094368 A1 | 4/2010 | Halperin et al. |
| 2010/0114222 A1 * | 5/2010 | Gunderson ............ A61N 1/37 607/8 |
| 2012/0029373 A1 * | 2/2012 | Stadler .................... A61N 1/37 600/515 |
| 2013/0079861 A1 | 3/2013 | Reinert et al. |
| 2013/0131750 A1 * | 5/2013 | Stadler ................. A61N 1/3627 607/25 |
| 2013/0138006 A1 | 5/2013 | Bornzin et al. |
| 2015/0290467 A1 | 10/2015 | Ludwig |
| 2015/0306375 A1 | 10/2015 | Marshall et al. |
| 2015/0306410 A1 | 10/2015 | Marshall et al. |
| 2016/0106989 A1 | 4/2016 | Stadler et al. |
| 2016/0106991 A1 | 4/2016 | Stadler et al. |
| 2016/0158567 A1 | 6/2016 | Marshall et al. |
| 2017/0157399 A1 | 6/2017 | Anderson et al. |
| 2017/0312534 A1 | 11/2017 | Cao et al. |

OTHER PUBLICATIONS

C00012966.WOU4 (PCT/US2017/029379) PCT Notification of Transmittal of the International Search Report and the Written Opinion of the International Searching Authority, dated Jul. 6, 2017, 14 pages.

* cited by examiner

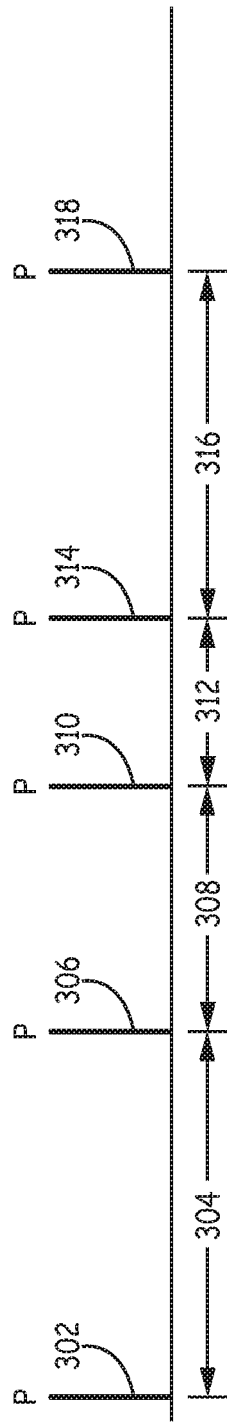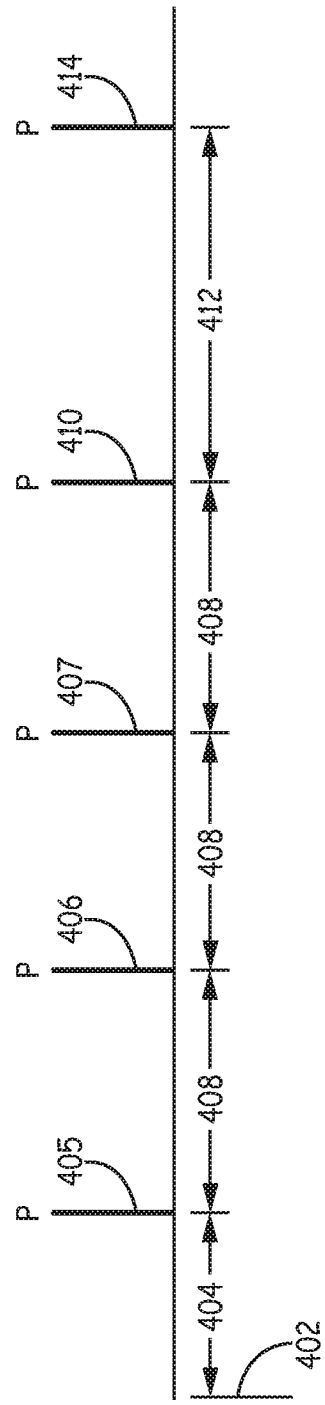

ASYSTOLE DETECTION AND RESPONSE IN AN IMPLANTABLE CARDIOVERTER DEFIBRILLATOR

CROSS REFERENCE TO RELATED APPLICATIONS

This application is a Continuation of U.S. patent application Ser. No. 15/142,074, filed Apr. 29, 2016, entitled "ASYSTOLE DETECTION AND RESPONSE IN AN IMPLANTABLE CARDIOVERTER DEFIBRILLATOR," which claims the benefit of the filing date of provisional U.S. Patent Application No. 62/328,803, filed Apr. 28, 2016, entitled "ASYSTOLE DETECTION AND RESPONSE IN AN IMPLANTABLE CARDIOVERTER DEFIBRILLATOR," the content of both of which is incorporated by reference in their entirety.

TECHNICAL FIELD

The disclosure relates generally to implantable medical devices and, in particular, to an implantable cardioverter defibrillator and method for detecting and responding to cardiac asystole.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to position electrodes or other sensors at desired locations for delivery of electrical stimulation or sensing of physiological conditions. For example, electrodes or sensors may be carried along a distal portion of a lead that is extended subcutaneously, submuscularly, or transvenously. A proximal portion of the lead may be coupled to an implantable medical device housing, which contains circuitry such as signal generation circuitry and/or sensing circuitry.

Some IMDs, such as cardiac pacemakers or implantable cardioverter defibrillators (ICDs), provide therapeutic electrical stimulation to the heart of the patient via electrodes carried by one or more implantable leads and/or the housing of the pacemaker or ICD. The leads may be transvenous, e.g., advanced into the heart through one or more veins to position endocardial electrodes in intimate contact with the heart tissue. Other leads may be non-transvenous leads implanted outside the heart, e.g., implanted epicardially, pericardially, or subcutaneously. The electrodes are used to deliver electrical pulses to the heart to address abnormal cardiac rhythms.

IMDs capable of delivering electrical pulses for treating abnormal cardiac rhythms typically sense signals representative of intrinsic depolarizations of the heart and analyze the sensed signals to identify the abnormal rhythms. Upon detection of an abnormal rhythm, the device may deliver an appropriate electrical stimulation therapy to restore a more normal rhythm.

SUMMARY

In general, the disclosure is directed to techniques for detecting a long ventricular pause or asystole and providing a response to the detected asystole by an ICD. An ICD operating according to the techniques disclosed herein operates in a sensing without pacing mode during which cardiac electrical signals are sensed but no pacing pulses are scheduled or delivered. The ICD may automatically switch to a pacing mode in response to detecting asystole during the sensing without pacing mode when automatic switching to a pacing mode is enabled. If the automatic switching is not enabled, the response to the asystole detection includes storing asystole episode data. If the automatic switching is enabled, the ICD may switch to a temporary pacing mode in some instances and to a permanent pacing mode in other instances. If the ICD automatically switches to the temporary pacing mode, the ICD returns to the sensing without pacing mode after a temporary pacing mode termination condition is satisfied.

In one example, the disclosure provides an ICD system comprising a sensing circuit configured to receive a cardiac electrical signal via a sensing electrode vector and sense cardiac events from the cardiac electrical signal, a therapy delivery circuit configured to deliver electrical pacing pulses to a patient's heart via a pacing electrode vector, and a control circuit coupled to the sensing circuit and the therapy delivery circuit and configured to automatically switch between a sensing without pacing mode and a temporary pacing mode. The control circuit is configured to detect asystole based on the cardiac electrical signal while operating in the sensing without pacing mode; in response to detecting the asystole, determine if asystole backup pacing is enabled, and automatically switch to the temporary pacing mode in response to the asystole backup pacing being enabled.

In another example, the disclosure provides a method performed by an ICD system. The method includes receiving a cardiac electrical signal by a sensing circuit of the ICD; detecting asystole by a control circuit of the ICD based on the cardiac electrical signal while operating in a sensing without pacing mode; in response to detecting the asystole, determining by the control module if asystole backup pacing is enabled, and automatically switching to a temporary pacing mode in response to the asystole backup pacing being enabled.

In another example, the disclosure provides a non-transitory, computer-readable storage medium comprising a set of instructions which, when executed by a control circuit of an ICD system, cause the system to receive a cardiac electrical signal by a sensing circuit of an ICD; detect asystole based on the cardiac electrical signal while operating in a sensing without pacing mode; in response to detecting the asystole, determine if asystole backup pacing is enabled, and automatically switch to a temporary pacing mode in response to the asystole backup pacing being enabled.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF THE DRAWINGS

FIG. 7 is a timing diagram of events during a pacing mode according to one example.

FIG. 8 is another timing diagram of events during a pacing mode according to another example.

DETAILED DESCRIPTION

In general, this disclosure describes techniques for detecting asystole and providing a response in an ICD. The techniques disclosed herein are used to control the operating mode of an ICD for detecting and responding to forms of bradycardia, such as a long ventricular pause or asystole. ICD patients often do not require chronic bradycardia pacing and frequent or prolonged single chamber ventricular pacing is generally undesirable. Some ICD patients, however, may experience asystole or long ventricular pauses as their disease progresses. The disclosed techniques may be implemented in an ICD to minimize cardiac pacing and promote intrinsically conducted heart rhythms in patient's receiving an ICD while still providing backup support for patients that experience long ventricular pauses or asystole or develop a need for bradycardia pacing after implantation of the ICD system. As disclosed herein, an ICD operates in a sensing without pacing mode and only switches to a bradycardia pacing mode when asystole or a long ventricular pause is detected following an intrinsic R-wave and automatic switching to a pacing mode is enabled.

The sensing without pacing mode and the temporary and permanent pacing modes described herein refer to operating modes for providing a response to bradycardia. It is recognized that tachyarrhythmia operating modes for detecting and responding to tachyarrhythmia may be operating in parallel to the bradycardia operating modes such that, for example, during the bradycardia sensing without pacing mode, bradycardia and asystole backup pacing pulses are not scheduled or delivered but pacing pulses may be delivered as part of a tachyarrhythmia therapy response to detecting tachycardia or fibrillation, including anti-tachycardia pacing (ATP) and/or post-shock pacing. Pacing pulses delivered in response to a fast ventricular rhythm or following a pacing shock delivered to terminate a tachyarrhythmia, however, are controlled according to programmed tachyarrhythmia operating mode and control parameters and are not controlled by a bradycardia operating mode.

As used herein, the term "sensing without pacing mode" refers to an operating mode that includes sensing of a cardiac electrical signal and detection of asystole and does not include scheduling or delivering any cardiac pacing pulses. However, it is recognized that a tachyarrhythmia therapy response may occur during the sensing without pacing mode which may include anti-tachycardia pacing or post-shock pacing, initiated due to a fast heart rate or delivering a cardioversion/defibrillation shock. During the sensing without pacing mode described herein, a slow heart rate, e.g., less than a programmed bradycardia lower pacing rate does not result in pacing pulse scheduling or delivery.

Figure 1A:
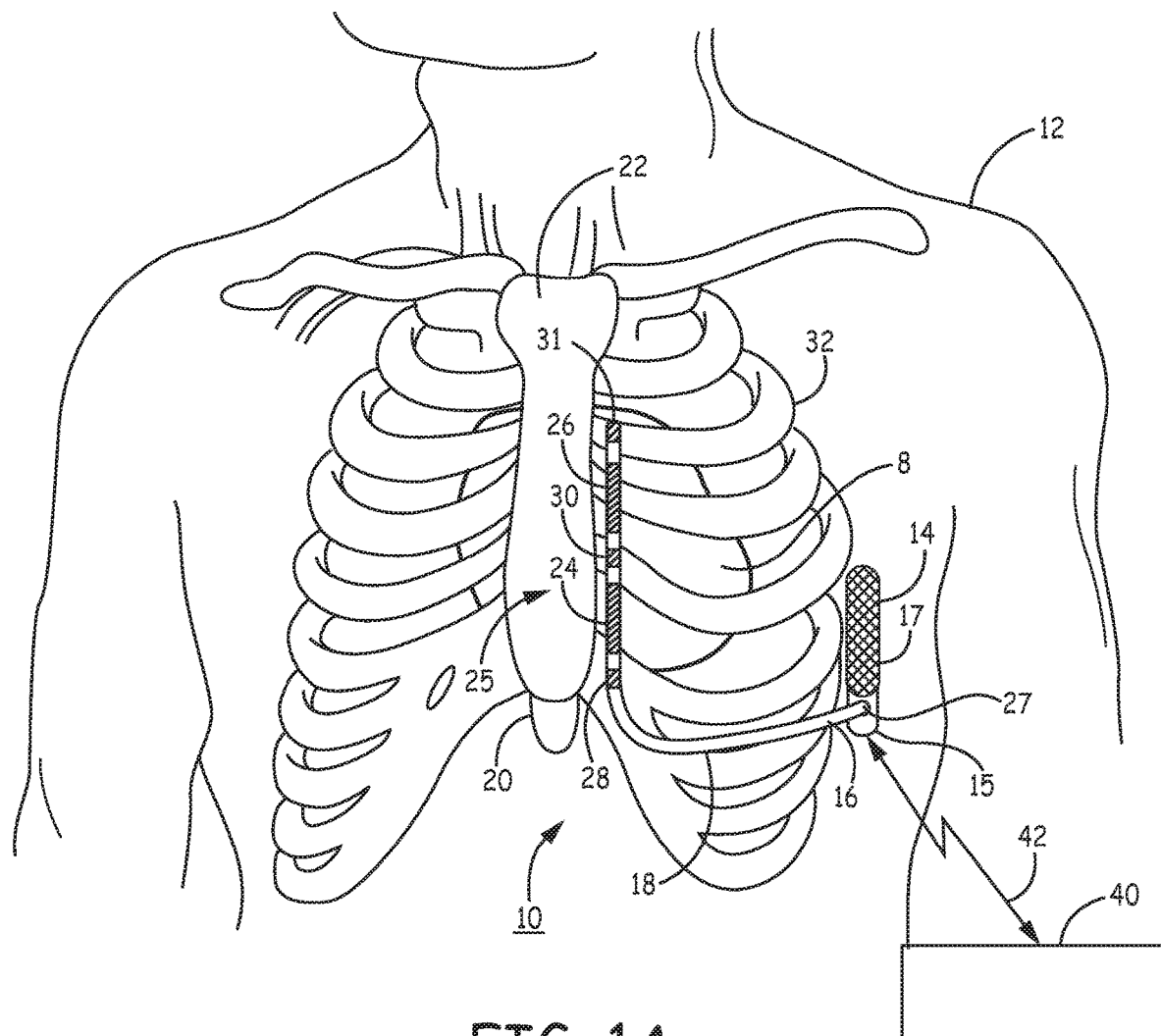
FIGS. 1A and 1B are conceptual diagrams of an extra-cardiovascular ICD system according to one example.
Figure 1B:
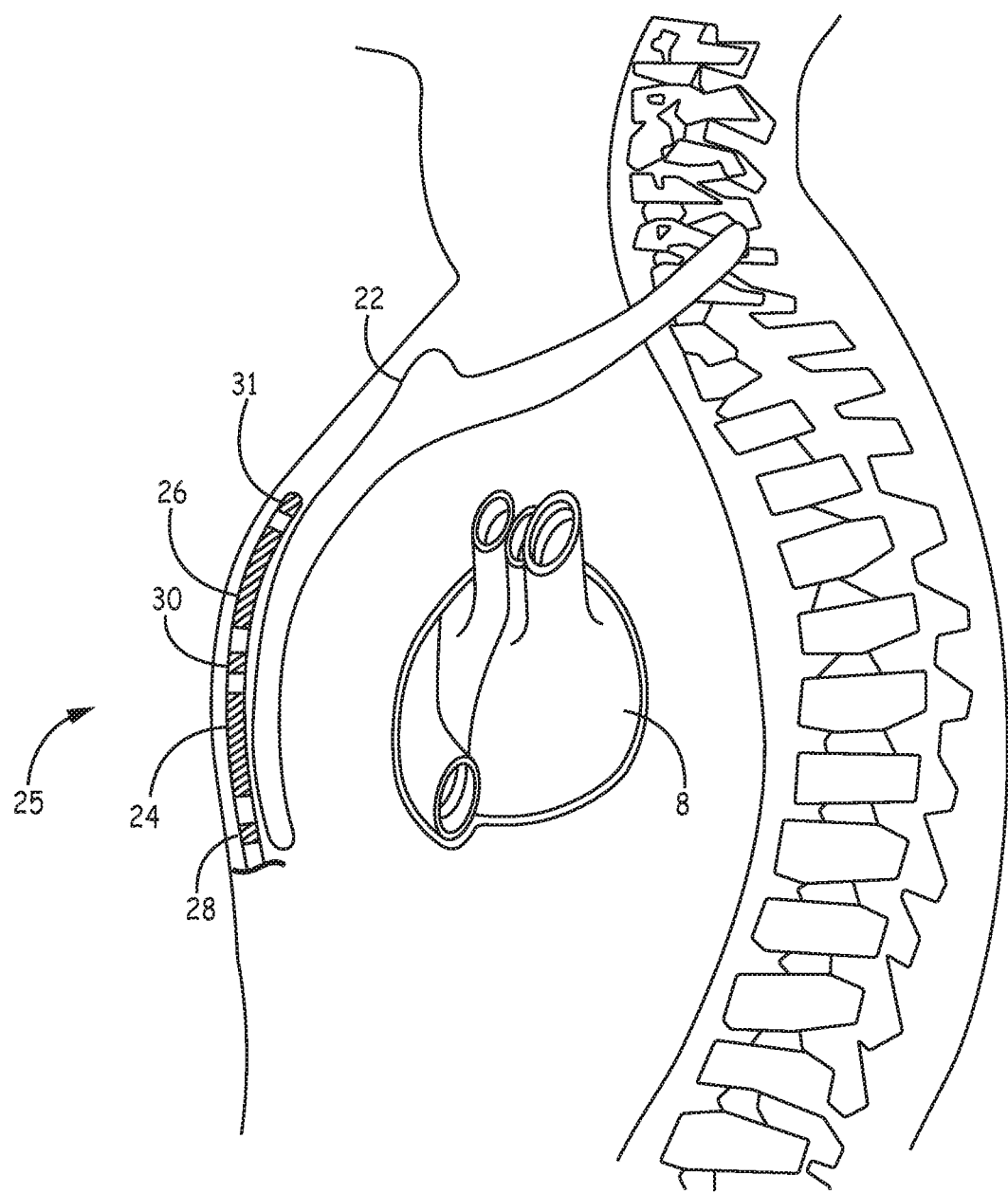

FIGS. 1A and 1B are conceptual diagrams of one example of an ICD system in which the techniques disclosed herein may be implemented. FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and pacing pulses.

As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue.

Extra-cardiovascular pacing pulses delivered by ICD 14 may be required to have relatively higher pulse energy in order to capture the patient's heart than pacing pulses delivered using endocardial or epicardial leads and electrodes. In order to conserve the battery charge of the extra-cardiovascular ICD system 10 for delivering cardioversion and defibrillation shocks, and promote an intrinsically conducted sinus rhythm over a paced rhythm, ICD 14 operates in a sensing without bradycardia pacing mode and only switches to a bradycardia pacing mode when asystole or a long ventricular pause is detected. Energy may also be conserved by not maintaining pacing capacitors in a charged state, ready for pacing pulse delivery, during the sensing without pacing mode. These techniques are disclosed in the context of an extra-cardiovascular ICD, such as system 10; however aspects of the techniques disclosed herein may be beneficially implemented in an ICD system that includes transvenous leads carrying endocardial electrodes or non-transvenous leads carrying epicardial electrodes as well. Generally, the techniques disclosed herein may be implemented in any ICD system for conserving battery longevity, promoting intrinsically conducted sinus rhythm and minimizing cardiac pacing while still providing the ability to provide cardiac pacing for the patient when asystole or a long ventricular pause occurs ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a can electrode). In examples described herein, housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses in conjunction with lead-based cathode electrodes and/or for sensing cardiac signals. In other instances, the housing 15 of ICD 14 may include a plurality of electrodes on an outer portion of the housing. The outer portion(s) of the housing 15 functioning as an electrode(s) may be coated with a material, such as titanium nitride. Housing 15 may be coated with an electrically insulating coating but have an exposed electrically conductive portion defining the can electrode.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memory, transceivers, sensors, electrical sensing circuitry, therapy delivery circuitry, power sources and other components for sensing cardiac electrical signals, detecting a heart rhythm, and controlling and delivering electrical stimulation pulses to treat an abnormal heart rhythm.

Lead 16 includes an elongated lead body 18 having a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead 16 includes defibrillation electrodes 24 and 26 and pace/sense electrodes 28, 30 and 31. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently. Electrodes 24 and 26 (and in some examples housing 15) are referred to herein as defibrillation electrodes because they are utilized, individually or collectively, for delivering high voltage stimulation therapy (e.g., cardioversion or defibrillation shocks and in some cases pacing pulses). Electrodes 24 and 26 may be elongated coil electrodes and generally have a relatively high surface area for delivering high voltage electrical stimulation pulses compared to low voltage pacing and sensing electrodes 28, 30 and 31. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. Electrodes 24 and/or 26 may be used in a pacing electrode vector for delivering extra-cardiovascular pacing pulses, such as backup asystole pacing pulses, bradycardia pacing pulses, anti-tachycardia pacing (ATP) pulses, post-shock pacing pulse, and/or in a sensing vector used to sense cardiac electrical signals and detect asystole, bradycardia, ventricular tachycardia (VT) and ventricular fibrillation (VF).

Electrodes 28, 30 and 31 are relatively smaller surface area electrodes for delivering low voltage pacing pulses and for sensing cardiac electrical signals. Electrodes 28, 30 and 31 are referred to as pace/sense electrodes because they are generally configured for use in low voltage applications, e.g., used as either a cathode or anode for delivery of pacing pulses and/or sensing of cardiac electrical signals. In some instances, electrodes 28, 30 and 31 may provide only pacing functionality, only sensing functionality or both.

In the example illustrated in FIGS. 1A and 1B, electrode 28 is located proximal to defibrillation electrode 24, and electrode 30 is located between defibrillation electrodes 24 and 26. A third pace/sense electrode 31 may be located distal to defibrillation electrode 26. Electrodes 28 and 30 are illustrated as ring electrodes, and electrode 31 is illustrated as a hemispherical tip electrode in the example of FIGS. 1A and 1B. However, electrodes 28, 30 and 31 may comprise any of a number of different types of electrodes, including ring electrodes, short coil electrodes, hemispherical electrodes, directional electrodes, segmented electrodes, or the like, and may be positioned at any position along the distal portion 25 of lead 16. Further, electrodes 28, 30 and 31 may be of similar type, shape, size and material or may differ from each other.

Lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIGS. 1A and 1B as being offset laterally from and extending substantially parallel to sternum 22, lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of lead 16 may depend on the location of ICD 14, the arrangement and position of electrodes carried by the lead distal portion 25, and/or other factors.

Electrical conductors (not illustrated) extend through one or more lumens of the elongated lead body 18 of lead 16 from the lead connector at the proximal lead end 27 to electrodes 24, 26, 28, 30 and 31 located along the distal portion 25 of the lead body 18. Lead body 18 may be tubular or cylindrical in shape. In other examples, the distal portion 25 (or all of) the elongated lead body 18 may have a flat, ribbon or paddle shape. The lead body 18 of lead 16 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The elongated electrical conductors contained within the lead body 18 are each electrically coupled with respective defibrillation electrodes 24 and 26 and pace/sense electrodes 28, 30 and 31. The respective conductors electrically couple the electrodes 24, 26, 28, 30 and 31 to circuitry, such as a therapy delivery circuit and/or a sensing circuit, of ICD 14 via connections in the connector assembly 17, including associated electrical feedthroughs crossing housing 15. The electrical conductors transmit therapy from a therapy circuit within ICD 14 to one or more of defibrillation electrodes 24 and 26 and/or pace/sense electrodes 28, 30 and 31 and transmit sensed electrical signals from one or more of defibrillation electrodes 24 and 26 and/or pace/sense electrodes 28, 30 and 31 to the sensing circuit within ICD 14.

ICD 14 may obtain electrical signals corresponding to electrical activity of heart 8 via a combination of sensing vectors that include combinations of electrodes 28, 30, and/or 31. In some examples, housing 15 of ICD 14 is used in combination with one or more of electrodes 28, 30 and/or 31 in a sensing electrode vector. ICD 14 may even obtain cardiac electrical signals using a sensing vector that includes one or both defibrillation electrodes 24 and/or 26, e.g., between electrodes 24 and 26 or one of electrodes 24 or 26 in combination with one or more of electrodes 28, 30, 31, and/or the housing 15.

ICD 14 analyzes the cardiac electrical signals received from one or more of the sensing vectors to monitor for abnormal rhythms, such as asystole, bradycardia, ventricular tachycardia (VT) or ventricular fibrillation (VF). ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated by reference herein in its entirety.

ICD 14 generates and delivers electrical stimulation therapy in response to detecting a tachyarrhythmia (e.g., VT or VF) according to a tachyarrhythmia operating mode. ICD 14 may deliver ATP in response to VT detection, and in some cases may deliver ATP prior to a CV/DF shock or during high voltage capacitor charging in an attempt to avert the need for delivering a CV/DF shock. ATP may be delivered using an extra-cardiovascular pacing electrode vector selected from any of electrodes 24, 26, 28, 30, 31 and/or housing 15.

In addition to delivering electrical stimulation therapy for treating VT and VF according to a tachyarrhythmia operating mode, ICD 14 is configured to operate in a sensing without pacing mode according to a bradycardia operating mode and deliver bradycardia pacing support when automatic switching to a pacing mode is enabled. ICD 14 switches from the sensing without pacing mode to a pacing mode in response to detecting asystole or a long ventricular pause. Upon switching to the pacing mode, the pacing electrode vector used to deliver cardiac pacing pulses may be the same or different than the sensing electrode vector used to sense cardiac electrical signals and detect asystole. In one example, cardiac electrical signals are sensed between pace/sense electrodes 28 and 30, and pacing pulses are delivered between pace/sense electrode 30 used as a cathode electrode and defibrillation electrode 24 used as a return anode electrode. In other examples, pacing pulses delivered according to a bradycardia operating mode, during a temporary pacing or permanent bradycardia pacing mode, may be delivered between pace/sense electrode 28 and either (or both) defibrillation electrode 24 or 26 or between defibrillation electrode 24 and defibrillation electrode 26. These examples are not intended to be limiting, and it is recognized that other sensing electrode vectors and pacing electrode vectors may be selected according to individual patient need and the available electrodes coupled to ICD 14.

FIGS. 1A and 1B are illustrative in nature and should not be considered limiting of the practice of the techniques disclosed herein. In other examples, lead 16 may include less than three pace/sense electrodes or more than three pace/sense electrodes and/or a single defibrillation electrode or more than two electrically isolated or electrically coupled defibrillation electrodes or electrode segments. The pace/sense electrodes 28, 30 and/or 31 may be located elsewhere along the length of lead 16. For example, lead 16 may include a single pace/sense electrode 30 between defibrillation electrodes 24 and 26 and no pace/sense electrode distal to defibrillation electrode 26 or proximal defibrillation electrode 24. Various example configurations of extra-cardiovascular leads and electrodes and dimensions that may be implemented in conjunction with the techniques disclosed herein are described in U.S. Publication No. 2015/0306375 (Marshall, et al.) and U.S. Publication No. 2015/0306410 (Marshall, et al.), both of which are incorporated herein by reference in their entirety.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferior from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from ICD 14 and to program operating parameters and algorithms in ICD 14 for controlling ICD functions. External device 40 may alternatively be embodied as a home monitor or hand held device. External device 40 may be used to program cardiac rhythm detection parameters and therapy control parameters used by ICD 14. Control parameters used to detect asystole, control bradycardia pacing mode switching, and control delivery of asystole backup pacing pulses according to techniques disclosed herein may be programmed into ICD 14 using external device 40.

Data stored or acquired by ICD 14, including physiological signals or associated data derived therefrom, results of device diagnostics, and histories of detected rhythm episodes and delivered therapies, may be retrieved from ICD 14 by external device 40 following an interrogation command. As described below, ICD 14 may determine and store asystole episode data, including a cardiac electrical signal segment, in response to detecting asystole. Asystole episode data stored by ICD 14 may be transmitted to external device 40 for review by a clinician. Additionally or alternatively, ICD 14 may transmit a patient or clinician alert or notification to external device 40 in response to detecting a predetermined number of asystole episodes. An asystole detection notification may be transmitted the first time the predetermined number of asystole episodes is reached since ICD 14 was most recently interrogated by external device 40, or another external device, and the notification may not be transmitted again until after the next interrogation session.

Figure 2A:
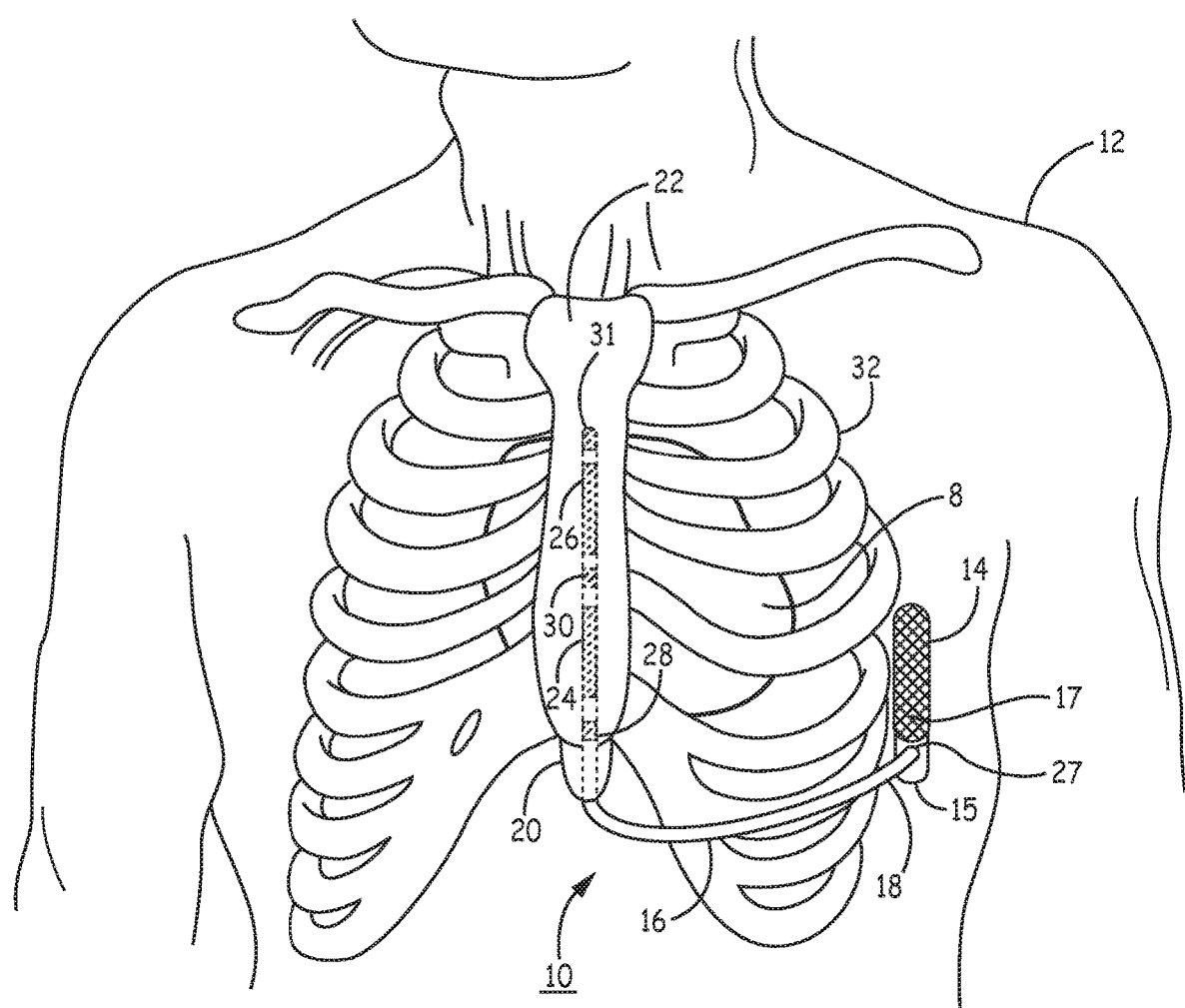
FIGS. 2A-2C are conceptual diagrams of a patient implanted with an ICD system in a different implant configuration than the arrangement shown in FIGS. 1A-1B.
Figure 2B:
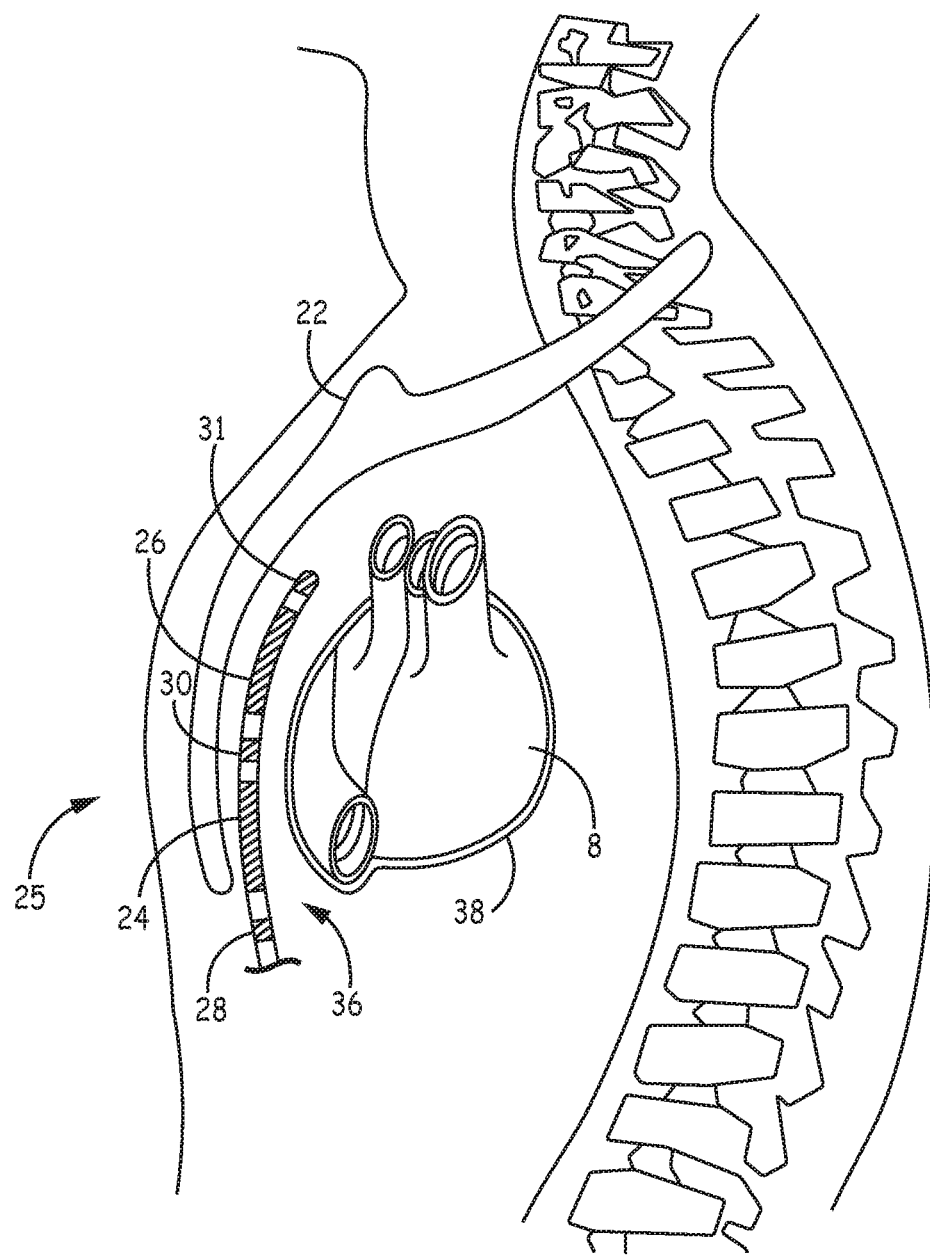
Figure 2C:
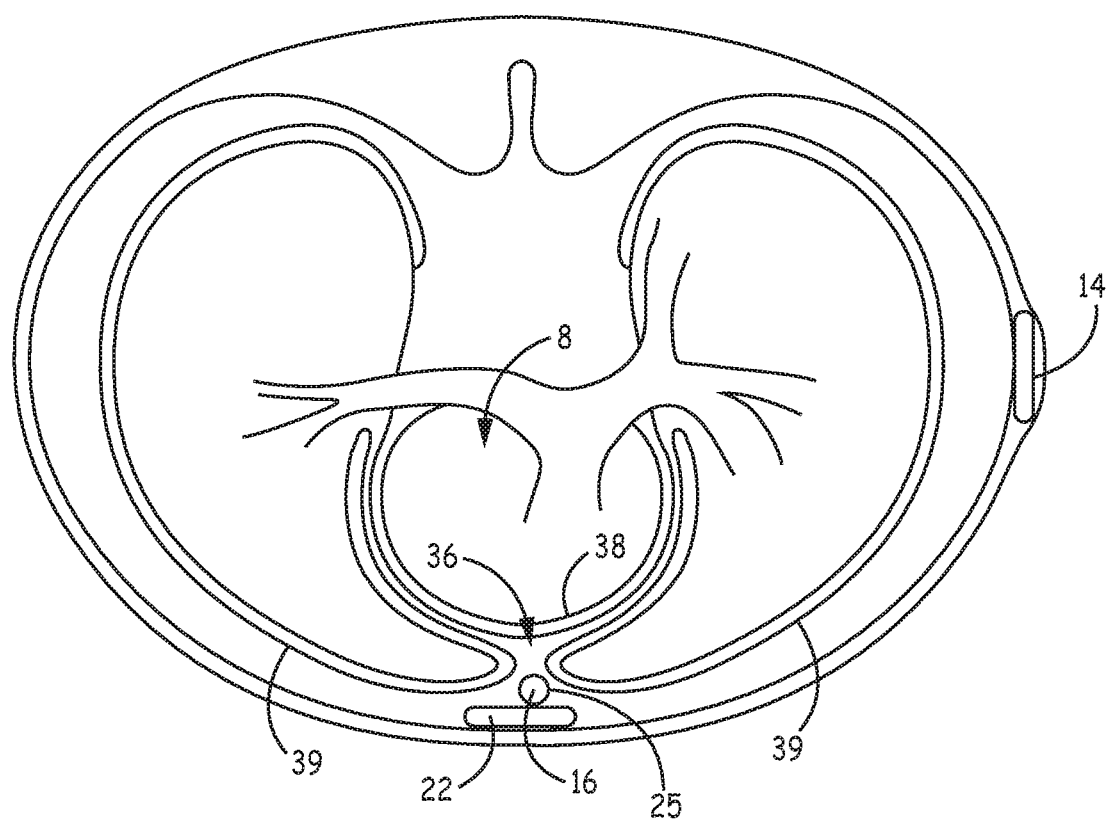

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis muscle and one or more costal cartilages. Anterior mediastinum 36 includes a quantity of loose connective tissue (such as areolar tissue), adipose tissue, some lymph vessels, lymph glands, substernal musculature, small side branches of the internal thoracic artery or vein, and the thymus gland. In one example, the distal portion 25 of lead 16 extends along the posterior side of sternum 22 substantially within the loose connective tissue and/or substernal musculature of anterior mediastinum 36.

A lead implanted such that the distal portion 25 is substantially within anterior mediastinum 36 may be referred to as a "substernal lead." In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to but typically not within the pericardium 38 of heart 8. Other implant locations and lead and electrode arrangements that may be used in conjunction with the cardiac pacing techniques described herein are generally disclosed in the above-incorporated patent applications.

Figure 3:
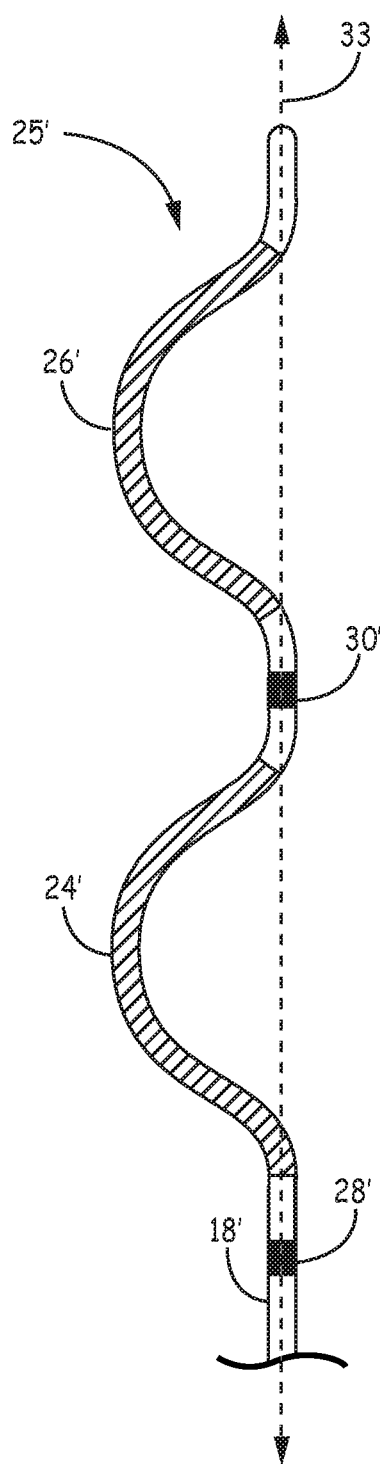
FIG. 3 is a conceptual diagram illustrating a distal portion of another example of the extra-cardiovascular lead of FIGS. 1A-2C.

FIG. 3 is a conceptual diagram illustrating a distal portion 25' of another example of extra-cardiovascular lead 16 of FIGS. 1A-2C having a curving distal portion 25' of lead body 18'. Lead body 18' may be formed having a curving, bending, serpentine, or zig-zagging shape along distal portion 25'. In the example shown, defibrillation electrodes 24' and 26' are carried along curving portions of the lead body 18'. Pace/sense electrode 30' is carried in between defibrillation electrodes 24' and 26'. Pace/sense electrode 28' is carried proximal to the proximal defibrillation electrode 24'. No electrode is provided distal to defibrillation electrode 26' in this example.

As shown in FIG. 3, lead body 18' may be formed having a curving distal portion 25' that includes two "C" shaped curves, which together may resemble the Greek letter epsilon, "ϵ." Defibrillation electrodes 24' and 26' are each carried by one of the two respective C-shaped portions of the lead body distal portion 25', which extend or curve in the same direction away from a central axis 33 of lead body 18'. In the example shown, pace/sense electrode 28' is proximal to the C-shaped portion carrying electrode 24', and pace/sense electrode 30' is proximal to the C-shaped portion carrying electrode 26'. Pace/sense electrodes 28' and 30' may, in some instances, be approximately aligned with the central axis 33 of the straight, proximal portion of lead body 18' such that mid-points of defibrillation electrodes 24' and 26' are laterally offset from electrodes 28' and 30'. Other examples of extra-cardiovascular leads including one or more defibrillation electrodes and one or more pacing and sensing electrodes carried by curving, serpentine, undulating or zig-zagging distal portion of the lead body that may be implemented with the pacing techniques described herein are generally disclosed in U.S. patent application Ser. No. 14/963,303, incorporated herein by reference in its entirety.

Figure 4:
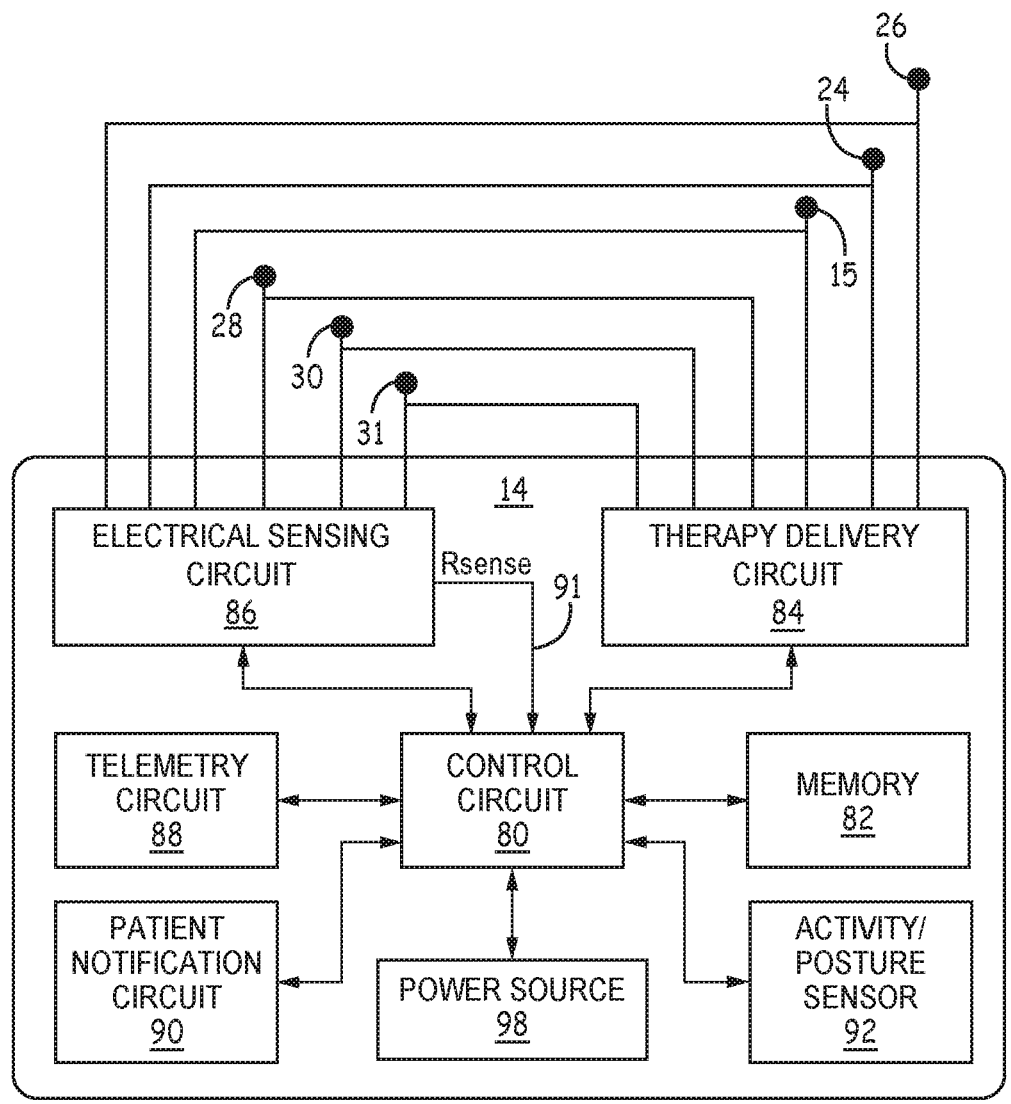
FIG. 4 is a schematic diagram of the ICD of FIGS. 1A-2C according to one example.

FIG. 4 is a schematic diagram of ICD 14 according to one example. The electronic circuitry enclosed within housing 15 (shown schematically as an electrode in FIG. 4) may include software, firmware and/or hardware that cooperatively monitor one or more cardiac electrical signals, determine when an electrical stimulation therapy is necessary, and deliver therapies as needed according to programmed therapy delivery algorithms and control parameters. The software, firmware and/or hardware are configured to monitor a cardiac electrical signal for detecting an abnormal heart rhythm and configured to select and deliver an appropriate electrical stimulation therapy for treating the abnormal rhythm. ICD 14 is coupled to an extra-cardiovascular lead, such as lead 16 carrying extra-cardiovascular electrodes 24, 26, 28, 30 and 31, for delivering electrical stimulation pulses to the patient's heart and for sensing cardiac electrical signals.

ICD 14 includes a control circuit 80, memory 82, therapy delivery circuit 84, cardiac electrical signal sensing circuit 86, telemetry circuit 88, patient notification circuit 90 and sensor 92. A power source 98 provides power to the circuitry of ICD 14, including each of the components 80, 82, 84, 86, 88, 90 and 92 as needed. Power source 98 may include one or more energy storage devices, such as one or more rechargeable or non-rechargeable batteries. The connections between power source 98 and each of the other components 80, 82, 84, 86, 88, 90 and 92 are to be understood from the general block diagram of FIG. 4, but are not shown for the sake of clarity. For example, power source 98 may be coupled to a low voltage charging circuit and to a high voltage charging circuit included in therapy delivery circuit 84 for charging low voltage and high voltage capacitors, respectively, included in therapy delivery circuit 84 for producing respective low voltage pacing pulses, such as asystole backup pacing pulses, bradycardia pacing pulses, post-shock pacing or ATP pulses, or for producing high voltage pulses, such as CV/DF shock pulses, and in some cases high voltage pacing pulses. In some examples, high voltage capacitors are charged and utilized for delivering pacing pulses for providing asystole backup pacing instead of low voltage capacitors. Power source 98 additionally powers one or more processors and/or other control circuits included in control circuit 80 as well as other components of sensing circuit 86, telemetry circuit 88, memory 82, and therapy delivery circuit 84 as needed.

The functional blocks shown in FIG. 4 represent functionality included in ICD 14 and may include any discrete and/or integrated electronic circuit components that implement analog and/or digital circuits capable of producing the functions attributed to ICD 14 herein. The various components may include an application specific integrated circuit (ASIC), an electronic circuit, a processor (shared, dedicated, or group) and memory that execute one or more software or firmware programs, a combinational logic circuit, state machine, or other suitable components or combination of any of the aforementioned components that provide the described functionality. The particular form of software, hardware and/or firmware employed to implement the functionality disclosed herein will be determined primarily by the particular system architecture employed in the device and by the particular detection and therapy delivery methodologies employed by the ICD 14. Providing software, hardware, and/or firmware to accomplish the described functionality in the context of any modern ICD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. For example, memory 82 may include read-only memory (ROM) in which stored programs controlling the operation of the control circuit 80 reside. Memory 82 may further include random access memory (RAM) or flash memory configured as a number of recirculating buffers capable of holding a series of measured intervals for analysis by the control circuit 80 for predicting or diagnosing an arrhythmia. Furthermore, memory 82 may include non-transitory computer readable media storing instructions that, when executed by one or more processing circuits, cause control circuit 80 or other ICD components to perform various functions attributed to ICD 14 or those ICD components. The non-transitory computer-readable media storing the instructions may include any of the media listed above.

The functions attributed to ICD 14 herein may be embodied as one or more integrated circuits. Depiction of different features as components is intended to highlight different functional aspects and does not necessarily imply that such components must be realized by separate hardware, firmware or software components. Rather, functionality associated with one or more components may be performed by separate hardware, firmware or software components, or integrated within common hardware, firmware or software components. For example, therapy delivery operations may be performed by therapy delivery circuit 84 under the control of control circuit 80 and may include operations implemented in a processor executing instructions stored in memory 82 and control signals such as timing signals, pacing pulse amplitude signals, and pacing electrode vector selection signals sent from control circuit 80 to therapy delivery circuit 84.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, and 30 (and 31 if present) carried by lead 16 (e.g., as shown in FIG. 1A) and the housing 15, which may function as a common or ground electrode for delivering electrical pulses or as an active can electrode for delivering CV/DF shock pulses.

Cardiac electrical signal sensing circuit 86, also referred to herein as "electrical signal sensing circuit" or simply "sensing circuit," may be selectively coupled to electrodes 28, 30 (and 31 if present) and/or housing 15 in order to monitor electrical activity of the patient's heart. Electrical signal sensing circuit 86 may additionally be selectively coupled to defibrillation electrodes 24 and/or 26 for use in a sensing electrode vector. Sensing circuit 86 is enabled to selectively monitor one or more sensing vectors at a time selected from the available electrodes 24, 26, 28, 30, 31 and housing 15. For example, sensing circuit 86 may include switching circuitry for selecting which of electrodes 24, 26, 28, 30 and 31 (shown in FIG. 1) and housing 15 are coupled to sense amplifiers or other cardiac event detection circuitry included in sensing circuit 86. Switching circuitry may include a switch array, switch matrix, multiplexer, or any other type of switching device suitable to selectively couple components of sensing circuit 86 to selected electrodes. In some instances, control circuit 80 may control the switching circuitry to selectively couple sensing circuit 86 to one or more sense electrode vectors. The cardiac event detection circuitry within sensing circuit 86 may include one or more sense amplifiers, filters, rectifiers, voltage amplitude threshold detectors, comparators, analog-to-digital converters (ADCs), or other analog or digital components.

In some examples, sensing circuit 86 includes multiple sensing channels for acquiring cardiac electrical signals from multiple sensing vectors selected from electrodes 24, 26, 28, 30 (and 31 if present) and housing 15. Each sensing channel may be configured to amplify, filter and rectify the cardiac electrical signal received from selected electrodes coupled to the respective sensing channel to improve the signal quality for sensing cardiac events, e.g., R-waves. For example, each sensing channel may include a pre-filter and amplifier for filtering and amplifying a signal received from a selected pair of electrodes. The resulting raw cardiac electrical signal may be passed from the pre-filter and amplifier to cardiac event detection circuitry for sensing cardiac events from the received cardiac electrical signal. Cardiac event detection circuitry may include a rectifier, post-filter and amplifier, a sense amplifier, comparator, and/or analog-to-digital converter for detecting a cardiac event when the cardiac electrical signal crosses a sensing threshold. The sensing threshold may be set by control circuit 80, based on a value stored in memory 82 which may be programmed by a user, and passed from control circuit 80 to sensing circuit 86 via a data bus. Sensing circuit 86 may include an auto-adjusting sense amplifier or detector that compares the cardiac signal to a sensing threshold that decays or decreases from a starting value to a minimum sensing floor in some examples.

Upon detecting a cardiac event, sensing circuit 86 may produce a sensed event signal, such as an R-wave sensed event signal 91, that is passed to control circuit 80. The sensed event signals 91 are used by control circuit 80 for detecting cardiac rhythms and determining a need for therapy. Electrical signal sensing circuit 86 may also pass a digitized electrocardiogram (ECG) signal to control circuit 80 for morphology analysis performed for detecting and discriminating heart rhythms.

Additionally or alternatively, electrical signals received by sensing circuit 86 from a selected sensing electrode vector may be passed through a bandpass filter and amplifier, provided to a multiplexer and thereafter converted to multi-bit digital signals by an analog-to-digital converter, all included in sensing circuit 86, for storage in random access memory or flash memory included in memory 82 under control of a direct memory access circuit via a data/address bus. The digitized cardiac electrical signal may be analyzed by control circuit 80 for identifying cardiac events such as R-waves and for detecting and discriminating abnormal rhythms, such as asystole, VT and VF.

Control circuit 80 may be a microprocessor-based controller that employs digital signal analysis techniques to characterize the digitized signals stored in memory 82 to recognize and classify the patient's heart rhythm employing any of numerous signal processing methodologies for analyzing cardiac signals and cardiac event waveforms, e.g., R-waves. One tachyarrhythmia detection system is described in U.S. Pat. No. 5,545,186 (Olson et al.), incorporated herein by reference in its entirety.

Therapy delivery circuit 84 includes charging circuitry, one or more charge storage devices, such as one or more high voltage capacitors and/or one or more low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Control circuit 80 may include various timers or counters that control when pacing pulses are delivered.

For example, control circuit 80 may include pacer timing and control circuitry having programmable digital counters set by the microprocessor of the control circuit 80 for controlling the basic time intervals associated with various pacing modes or anti-tachycardia pacing sequences delivered by ICD 14. The microprocessor of control circuit 80 may also set the amplitude, pulse width, polarity or other characteristics of the cardiac pacing pulses, which may be based on programmed values stored in memory 82.

During a pacing mode, escape interval counters within the pacer timing and control circuitry are reset upon sensing of R-waves as indicated by signals 91 from sensing circuit 86. When the escape interval times out, a pacing pulse is generated by a pulse output circuit of therapy delivery circuit 84. The pace output circuit is coupled to the desired electrodes via switch matrix for discharging one or more capacitors across the pacing load. The escape interval counters are reset upon generation of pacing pulses, and thereby control the basic timing of cardiac pacing functions, including asystole backup pacing during a temporary pacing mode, permanent bradycardia pacing modes, and ATP or post-shock pacing controlled according to a tachyarrhythmia operating mode. The durations of the escape intervals are determined by control circuit 80 via a data/address bus. The value of the count present in the escape interval counter when reset by a sensed R-wave can be used to measure an RR interval as the time interval between two consecutively sensed R-waves. RR intervals are determined for detecting the occurrence of a variety of arrhythmias and for storing RR interval data associated with a detected arrhythmia episode, including asystole episodes.

In some examples, control circuit 80 may detect asystole when operating in a sensing without pacing mode when a counter or timer started upon receiving an R-wave sensed event signal 91 reaches or times out a predetermined asystole detection time interval, such as an interval of 2 seconds, an interval of 3 seconds or an interval of 4 seconds or more. The asystole detection time interval used for detecting asystole by control circuit 80 may be programmable and stored in memory 82 and may be up to six seconds long in some examples. Other techniques may be implemented for detecting asystole. For example, aspects disclosed in U.S. Pat. No. 8,831,713 (Stadler, et al.), incorporated herein by reference in its entirety, may be employed for detecting asystole and avoiding false asystole detection. In response to detecting asystole, control circuit 80 switches to a pacing mode if asystole backup pacing is enabled and controls therapy delivery circuit 84 to deliver pacing pulses according to programmed pacing escape intervals in the absence of an R-wave sensed event signal.

Therapy delivery circuit 84 may be controlled by control circuit 80 to deliver pacing pulses via a pacing electrode vector selected from the extra-cardiovascular electrodes 24, 26, 28, 30 (and 31 if present) and/or housing 15 using a high voltage output circuit capable of also delivering cardioversion and defibrillation shocks. The pacing pulse may be delivered as a single pulse, which may be a balanced biphasic pulse in some instances, by enabling the high voltage output circuit to deliver a pacing pulse that is much lower in energy than a cardioversion/defibrillation shock. Enabling the high-voltage pacing output circuit of therapy delivery circuit 84 to deliver a pacing pulse during a temporary pacing mode enabled in response to detecting asystole may include setting a variable shunt resistance included in the high voltage output circuit to maintain a minimum electrical current to switches included in the high voltage pacing output circuit, e.g., in an H-bridge, used to couple previously charged high voltage capacitor(s) to the pacing electrode vector for delivery of the pacing pulse. The variable resistance may be set to match a pacing load so that electrical current through the switches may be maintained at or above a minimum electrical current required to maintain a stable closed state of desired switches during the pacing pulse. Techniques for delivering the pacing pulse using a high voltage output circuit of therapy delivery circuit 84 are generally disclosed in provisionally-filed U.S. Pat. Application No. 62/262,499 (Anderson, et al.), incorporated herein by reference in its entirety.

In some examples, therapy delivery circuit 84 may include a low voltage output circuit for delivering pacing pulses during a temporary or permanent bradycardia pacing mode, as well as for post-shock pacing, ATP or other pacing pulses. The low voltage output circuit may include a low voltage capacitor array for delivering pacing pulses. Control circuit 80 may select a combination of capacitors from the capacitor array so that an RC time constant based on the pacing electrode vector impedance and the selected capacitors results in a pacing pulse width that is long enough to capture when the pacing pulse amplitude is less than a pain threshold of the patient. By selecting a capacitor combination that has an RC time constant that results in a relatively slow decay rate of the pulse, the pacing pulse amplitude at truncation of the pacing pulse after a relatively long pulse width, e.g., 1.5 ms or longer, is still greater than the pacing capture threshold of the heart. Extra-cardiovascular pacing may be delivered at a pacing pulse amplitude below a pain threshold of the patient with a pulse width long enough to deliver adequate energy to successfully pace the heart. ICD 14 may be configured to deliver pacing pulses using extra-cardiovascular electrodes according to the techniques generally disclosed in U.S. patent application Ser. No. 14/957, 651 (Christie, et al.), incorporated herein by reference in its entirety.

In other examples, therapy delivery circuit 84 may include a low voltage output circuit including at least two holding capacitors or at least two holding capacitor combinations that are charged by the low voltage charging circuit to a pacing pulse amplitude under the control of control circuit 80 and discharged sequentially to deliver at least two individual pulses that are fused in time to produce a composite pacing pulse having a total pulse width that is longer than the pulse width capture threshold of the heart. A series of fused low voltage electrical pulses may be delivered using extra-cardiovascular electrodes 24, 26, 28, and/or 30 (and 31 if available) and/or housing 15 to produce a composite cardiac pacing pulse having a total pulse width defined by the fused low voltage pulses. Extra-cardiovascular pacing pulses may be delivered by therapy delivery circuit 84 at a pacing pulse amplitude below a pain threshold of the patient and a total pulse width defined by the composite pacing pulse that is long enough to deliver adequate energy to successfully capture and pace the heart. Techniques for delivering fused pacing pulses using extra-cardiovascular electrodes that may be coupled to ICD 14 are generally disclosed in provisionally-filed U.S. Pat. Application No. 62/262,412 (Anderson, et al.), incorporated herein by reference in its entirety. Therapy delivery circuit 84 may include other types of pacing output circuitry for delivering pacing pulses using either low voltage capacitors, high voltage capacitors or a combination of both. The methods for detecting asystole and controlling an asystole backup pacing mode and a sensing without pacing mode as described herein may be implemented in conjunction with a variety of pacing output circuits.

In other examples, when ICD 14 is coupled to transvenous leads carrying endocardial electrodes, pacing pulses may be delivered using a low-voltage pacing output circuit configured to deliver pacing pulses that are typically less than 2.0 ms in pulse width and less than 8.5 V in pulse amplitude.

In response to the detection of asystole during a sensing without pacing mode, a backup asystole pacing therapy may be delivered after switching to a temporary pacing mode by loading pacing control parameters, which may be stored within memory 82, from the microprocessor included in control circuit 80 into the pacer timing and control circuit according to the pacing pulse amplitude, pacing pulse width, and one or more pacing escape intervals for controlling the timing of the pacing pulses as described in conjunction with FIGS. 7 and 8, for example. In response to detecting a threshold number of asystole episodes during the sensing without pacing mode, bradycardia pacing pulses may be delivered after switching to a permanent bradycardia pacing mode. During the temporary pacing mode, or during the permanent bradycardia pacing mode, the pacer timing and control circuit may set an escape interval counter when an R-wave sensed event signal 91 is received by control circuit 80. If the escape interval expires without receiving another R-wave sensed event signal, therapy delivery circuit 84 is enabled to discharge one or more capacitors across the selected pacing electrode vector.

In response to detection of a tachyarrhythmia, ATP pulses may be delivered by therapy delivery circuit 84 under the control of control circuit 80 according to a programmed ATP therapy sequence stored in memory 82. In the event that higher voltage cardioversion or defibrillation pulses are required, the control circuit microprocessor activates cardioversion and defibrillation control circuitry included in control circuit 80 to initiate charging of the high voltage capacitors via a charging circuit, both included in therapy delivery circuit 84, under the control of a high voltage charging control line. The voltage on the high voltage capacitors is monitored via a voltage capacitor line, which is passed to control circuit 80. When the voltage reaches a predetermined value set by the microprocessor of control circuit 80, a logic signal is generated on a capacitor full line passed to therapy delivery circuit 84, terminating charging. The defibrillation or cardioversion pulse is delivered to the heart under the control of the pacer timing and control circuitry by an output circuit of therapy delivery circuit 84 via a control bus. The output circuit determines the electrodes used for delivering the cardioversion or defibrillation pulse and the pulse wave shape. Therapy delivery and control circuitry generally disclosed in any of the above-incorporated patents may be implemented in ICD 14.

In some examples, ICD 14 includes a sensor 92 capable of producing a signal correlated to patient activity and/or patient posture. A signal from sensor 92 may be used to determine a sensor-indicated pacing rate that is used to control the rate of pacing pulses delivered by therapy delivery circuit 84 when rate responsive bradycardia pacing is enabled during a temporary or permanent pacing mode. Sensor 92 may be an accelerometer or other motion sensor. For instance, sensor 92 may be a one-dimensional, two-dimensional, or three-dimensional piezoelectric sensor or micro electro-mechanical systems (MEMS) sensor that generates a motion signal corresponding to acceleration or motion of the patient in one, two or three axes, respectively. Examples of a sensor and method for determining patient activity and posture are generally disclosed in U.S. Pat. No. 5,593,431 (Sheldon), incorporated herein by reference in its entirety. A piezoelectric accelerometer for detecting patient motion is disclosed, for example, in U.S. Pat. No. 4,485,813 (Anderson, et al.) and U.S. Pat. No. 5,052,388 (Sivula, et al.), both of which are incorporated herein by reference in their entirety. The use of a patient activity signal for providing rate-responsive pacing is generally disclosed in U.S. Pat. No. 7,031,772 (Condie, et al.), incorporated herein by reference in its entirety.

Control circuit 80 may be configured to determine one or more rest conditions from a signal received from sensor 92. One rest condition may be an activity state of the patient. Another rest condition may be a body posture of the patient. Control circuit 80 may be configured to determine whether the patient is in a rest state or a non-rest state based on the activity state of the patient, the body posture of the patient, and/or a time of day in some examples. Control circuit 80 may include a 24-hour timer or clock initialized to a time of day for determining the time of day.

In response to the patient activity determined from a signal from sensor 92 being below an activity threshold level, the patient body posture being in a non-upright posture (e.g., a lying or reclined position as opposed to a sitting, standing or walking position), and/or the time of day being night time, a resting state of the patient may be detected by control circuit 80. If the patient activity is greater than a threshold level, the patient is in an upright posture, and/or the time of day is daytime, control circuit 80 may detect a non-resting state of the patient. As described below in conjunction with FIGS. 9 and 10, the determined resting or non-resting state of the patient may be used to control asystole detection parameters, automatic switching to a temporary pacing mode for delivering asystole backup pacing pulses, and/or pacing control parameters used to control delivery of asystole backup pacing pulses after switching to a temporary pacing mode.

Control parameters utilized by control circuit 80 for detecting cardiac rhythms and controlling therapy delivery may be programmed into memory 82 via telemetry circuit 88. Telemetry circuit 88 includes a transceiver and antenna for communicating with external device 40 (shown in FIG. 1A) using RF communication as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12.

Control circuit 80 may terminate a temporary pacing mode that has been started upon asystole detection in response to a user command transmitted to ICD 14 from external device 40. Telemetry circuit 88 receives the command and passes command signal data to control circuit 80 for terminating the temporary pacing mode. Control circuit 80 may include a reed switch or Hall-effect sensor that may be activated by a user externally applying a magnet over ICD 14. Control circuit 80 may terminate the temporary pacing mode that was started upon asystole detection when a magnet being applied to the ICD 14 is detected based on the status of a Hall-effect sensor or reed switch or another magnet detection element included in control circuit 80. When the temporary pacing mode is terminated, control circuit 80 restores the sensing without pacing mode.

In some examples, the ICD 14 may be equipped with a patient notification circuit 90 that generates a signal perceivable by the patient to notify the patient of an important clinical event or ICD status that may warrant medical attention. For instance, control circuit 80 may control patient notification circuit 90 to issue an audible alert in response to detecting asystole. Any patient notification method used in implantable medical devices may be implemented in notification circuit 90 such as generating a perceivable twitch stimulation or an audible sound. A patient notification system may include an audio transducer that emits audible sounds including voiced statements or musical tones stored in memory 82 corresponding to a notification triggering event, such as an asystole episode. A patient notification system is generally described in U.S. Pat. No. 6,067,473 (Greeninger et al.), incorporated herein by reference in its entirety.

Figure 5A:
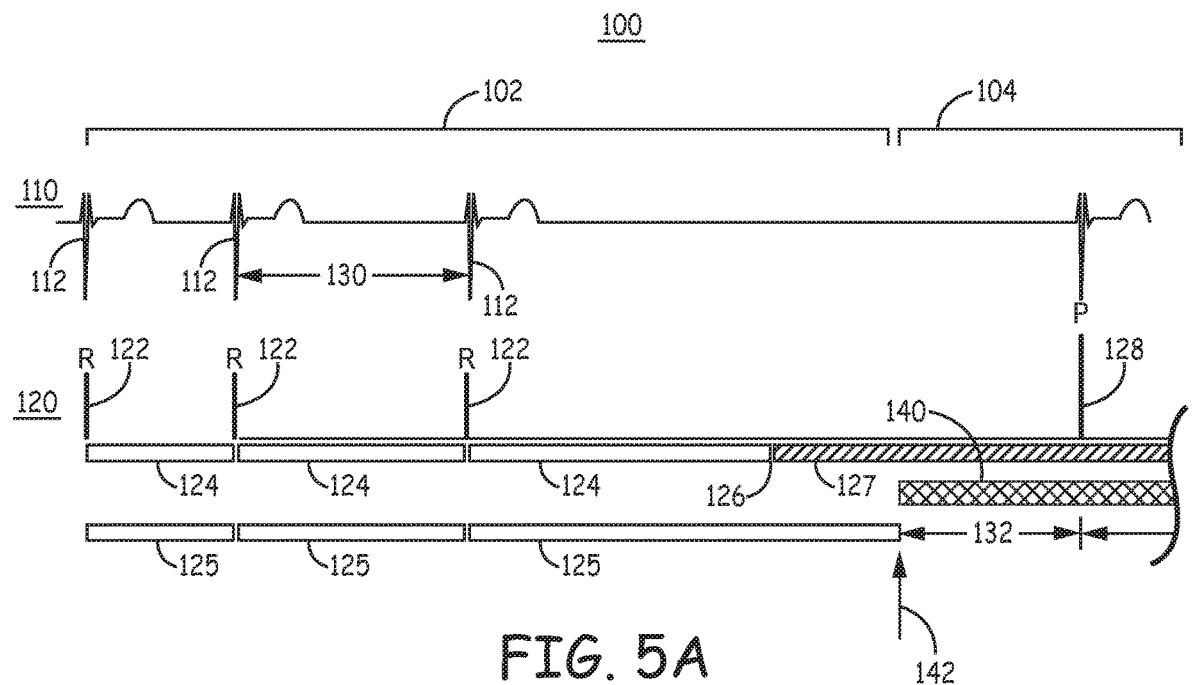
FIG. 5A and FIG. 5B are diagrams of a cardiac electrical signal and a corresponding cardiac event timeline depicting R-wave sensed event signals and pacing pulses generated by an ICD.
Figure 5B:
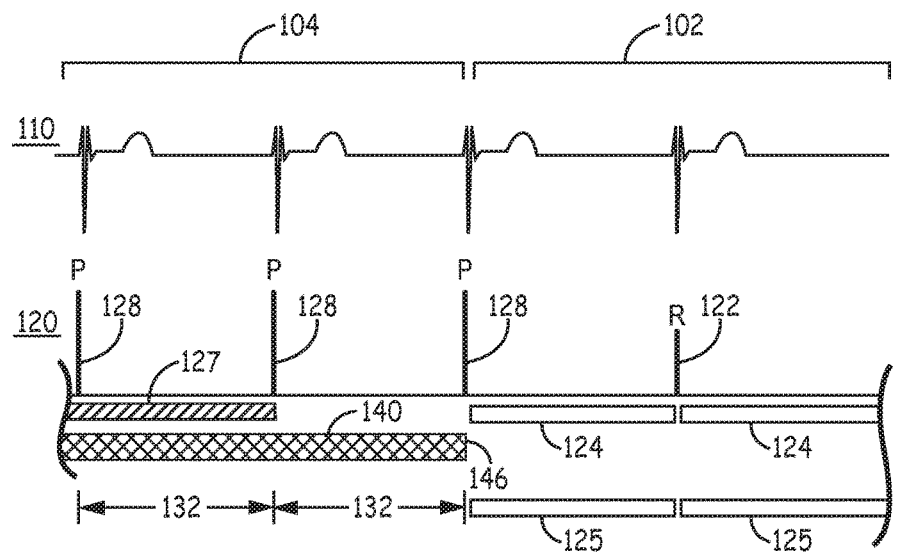

FIG. 5A and FIG. 5B are diagrams of a cardiac electrical signal 110 and a corresponding cardiac event timeline 120 depicting R-wave sensed event signals (R) 122 and pacing pulses (P) 128 generated by ICD 14. As shown in FIG. 5A, cardiac electrical signal 110 includes R-waves 112 that are sensed by the sensing circuit 86 of ICD 14. During a sensing without pacing mode 102, sensing circuit 86 produces an R-wave sensed event signal 122 that is passed to control circuit 80 each time a respective R-wave 112 is sensed.

In response to each R-wave sensed event signal 122, control circuit 80 may start a probable asystole time interval 124 and an asystole detection time interval 125. One or both of the probable asystole time interval 124 and the asystole detection time interval 125 may be programmable and may be set to the same or different time intervals. Both are reset upon an R-wave sensed event signal 122. If the probable asystole time interval 124 expires at time 126, before being reset due to an R-wave sensed event signal 122, the control circuit 80 enables asystole episode data storage at time 126. Asystole episode data storage may include storing a segment 127 of cardiac signal 122. The segment 127 of cardiac electrical signal 122 that is stored in memory 82 may extend from time 126 or a predetermined interval prior to the expiration of the probable asystole timer 124 to include cardiac events leading up to the asystole and may extend a predetermined time interval after the expiration of the probable asystole timer 124, after an asystole detection is made at time 142, or after switching to a temporary pacing mode 104 in response to detecting the asystole.

If the asystole detection time interval 125 expires without an R-wave sensed event signal 122, asystole is detected at time 142. In response to detecting asystole, control circuit 80 may switch from the sensing without pacing mode 102 to a temporary pacing mode 104. A pacing escape interval 132 is started upon switching to the temporary pacing mode 104, and pacing pulse 128 is delivered if the escape interval 132 expires without an R-wave sensed event signal occurring during the escape interval 132. The pacing escape interval 132 is set to a programmed asystole backup pacing rate interval, which may be the longest available pacing rate interval corresponding to a minimum available pacing rate. In other examples, the asystole backup rate interval used to set pacing escape interval 132 is set to be equal a programmed bradycardia pacing lower rate interval.

In some instances, instead of starting the first pacing escape interval 132 upon switching to the temporary pacing mode 104 at time 142, a pacing pulse may be immediately delivered upon switching to the temporary pacing mode 104, and the first pacing escape interval may be started after delivering the first pacing pulse. Charging of capacitors included in therapy delivery circuit 84 may begin after the probable asystole timer 124 expires so that a pacing pulse may be delivered immediately upon switching to the temporary pacing mode if asystole is detected. The pacing pulses delivered during the temporary pacing mode 104 may capture the ventricles of the patient's heart 8 and correspond to a VVI, VVIR, VVT or VVTR pacing mode. In some examples, a termination time interval 140 set to a predetermined maximum temporary pacing time period may be started upon switching to the temporary pacing mode 104.

In the VVI mode or VVIR mode (VVI plus rate responsive pacing), a pacing pulse is inhibited when an intrinsic R-wave is sensed during a pacing escape interval. In the VVT or VVTR mode, a sensed event triggers an immediate pacing pulse, which starts a pacing escape interval. The pacing pulse delivered immediately occurs in the physiological refractory period of the myocardium after the sensed event e.g., within 100 ms or within no more than 200 ms of the sensed event, and subsequent pacing pulses may be delivered at a rate that is faster than the intrinsic rate. This VVT or VVTR mode may be used in situations when P-wave oversensing or other false sensing of events as R-waves may be present. Oversensing of cardiac or non-cardiac noise may result in a pacing pulse being inhibited during a VVI(R) pacing mode. By using a VVT(R) pacing mode, inhibition of pacing pulses due to oversensed events that are not true R-waves is prevented.

To illustrate, when operating in a VVI mode, if control circuit 80 receives an R-wave sensed event signal from sensing circuit 86 during a pacing escape interval, e.g., the first pacing escape interval 132 shown in FIG. 5A, after switching to the temporary pacing mode 104, the first pacing pulse 128 shown in FIG. 5A would be inhibited (not delivered). The pacing escape interval 132 would be restarted without delivering the scheduled pacing pulse. When operating in a VVT mode, if control circuit 80 receives an R-wave sensed event signal during the first pacing escape interval 132 shown in FIG. 5A (or any other pacing escape interval) after switching to the temporary pacing mode 104, the scheduled pacing pulse 128 is triggered to be delivered immediately, before the pacing escape interval 132 expires so that the pacing pulse is delivered within a physiological refractory period of the sensed event. Delivery of the triggered pacing pulse causes the pacing escape interval 132 to be restarted.

Upon delivering a pacing pulse 128, the pacer timing and control circuitry included in control circuit 80 starts a next pacing escape interval 132 as shown in FIG. 5B. If an intrinsic R-wave is sensed during the next pacing escape interval 132, the pacing escape interval 132 is reset and the scheduled pacing pulse is inhibited when the pacing mode is VVI(R). If pacing escape interval 132 expires without sensing an intrinsic R-wave, however, a pacing pulse 128 is delivered by therapy delivery circuit 84. In other examples, an R-wave sensed event signal may trigger delivery of a pacing pulse when the temporary pacing mode is programmed to be a VVT(R) pacing mode. The pacing pulses 128 may all be delivered at the same pacing escape interval 132 in some cases. In other cases, as described below in conjunction with FIGS. 7 and 8, the pacing escape interval may be set to different values during the temporary pacing mode 104 such that pacing pulses may be delivered at different rates corresponding to the respective values of the pacing escape interval.

During the temporary pacing mode 104, control circuit 80 may continue writing a segment 127 of the cardiac electrical signal 110 to memory 82 to record the asystole episode and the pacing response. In other examples, the recorded segment 127 of the cardiac electrical signal 110 may terminate upon switching to the temporary pacing mode 104 or after a predetermined number of pacing pulses or other predetermined time limit. Control circuit 80 may monitor for one or more pacing mode termination conditions after switching to the temporary pacing mode 104. In one example, expiration of the termination time interval 140 is a temporary pacing mode termination condition. As such, upon expiration of the termination time interval 140 at 146, the control circuit 80 automatically switches from the temporary pacing mode 104 back to the sensing without pacing mode 102 as shown in FIG. 5B. Alternatively, control circuit 80 may include a counter for counting a predetermined maximum number of pacing pulses that can be delivered during the temporary pacing mode before switching back to the sensing without pacing mode. Other temporary pacing mode termination conditions are discussed below in conjunction with FIG. 6 and may include detecting a tachyarrhythmia episode, detecting a predetermined number of intrinsic R-waves, or upon a user request.

During the sensing without pacing mode 102, one or more RR intervals 130 may occur that are longer than the pacing escape interval 132 set to the asystole backup pacing interval during the temporary pacing mode 104. For example, pacing escape interval 132 may be set to a relatively long interval, such as 1.5 to 2 seconds, to provide asystole backup pacing at a minimal rate, e.g., 30 to 40 paces per minute. RR interval 130 may be greater than the pacing escape interval 132 but is less than the asystole detection time interval 124, which may be up to two seconds, up to three seconds, up to four seconds, or even up to 6 seconds or longer in some examples. Even when an RR interval 130 is longer than a programmed asystole backup rate interval, a bradycardia lower rate interval or other pacing interval used to set pacing escape interval timers during temporary pacing mode 104 or another bradycardia pacing mode, no pacing pulses are scheduled or delivered during the sensing without pacing mode. Bradycardia pacing pulses are not delivered during the sensing without pacing mode, however it is recognized that, if VT or VF is detected, ATP pulses or post-shock pacing pulses may be delivered during the sensing without pacing mode in accordance with programmed tachyarrhythmia therapy control parameters.

The first pacing pulse 128 shown in FIG. 5A is delivered during the temporary pacing mode 104, upon expiration of the first pacing escape interval 132 after switching to the temporary pacing mode, in this case a VVI temporary pacing mode. Pacing pulses may or may not be delivered after switching to the temporary pacing mode 104 depending on whether or not intrinsic R-waves are sensed during the first pacing escape interval 132 set upon switching to the temporary pacing mode (FIG. 5A) and in response to intrinsic R-waves sensed thereafter. In some instances, none or only the single, first pacing pulse 128 shown in FIG. 5A is delivered during the temporary pacing mode 104 due to intrinsic ventricular activity sensed prior to the expiration of all other pacing escape intervals set during the temporary pacing mode 104.

The pacing escape interval 132 may be set to an asystole backup rate interval, e.g., 2 seconds for an asystole backup pacing rate of 30 pulses per minute or 1.5 seconds for an asystole backup pacing rate of 40 pulses per minute. However, other asystole backup rate intervals may be used. In other examples, the pacing escape interval 132 may be set to a sensor-indicated pacing rate according to a rate responsive pacing mode, e.g., VVIR. Sensor 92 may provide a signal to control circuit 80. A sensor-indicated pacing rate is determined by control circuit 80 from the sensor signal and a rate transfer function stored in memory 82. Activity-based pacing rates may be determined as generally disclosed in the above-incorporated U.S. Pat. No. 7,031,772 (Condie, et al.). Other methods for using an accelerometer for monitoring patient activity for controlling pacing rate are generally disclosed in U.S. Pat. No. 5,562,711 (Yerich, et al.) and U.S. Pat. No. 6,449,508 (Sheldon, et al.), both of which are incorporated herein by reference.

In some examples, the pacing escape interval 132 may be controlled according to an asystole backup rate interval and a hysteresis interval. When the pacing escape interval 132 set to the asystole backup rate interval is restarted due to an R-wave sensed event signal 122 prior to expiration of the pacing escape interval 132, the pacing escape interval 132 is set to a hysteresis interval that is longer than the asystole backup rate interval to promote intrinsically conducted heart beats to occur without pacing. As long as the intrinsic heart rate is faster than the hysteresis rate, pacing is inhibited. If a hysteresis interval expires without a sensed intrinsic R-wave, a pacing pulse is delivered by the therapy delivery circuit 84 and the pacing escape interval 132 is set to the asystole backup rate interval. The first occurrence of an expired hysteresis time interval and delivered pacing pulse at the hysteresis rate may suspend hysteresis operations; control circuit 80 may reestablish the asystole backup rate interval as the pacing escape interval 132. Pacing pulses are delivered at a rate corresponding to the asystole backup rate interval until the temporary pacing mode is terminated or another R-wave sensed event signal is received by the control circuit 82, causing the pacing escape interval to be reset to the hysteresis interval. Examples of the use of a hysteresis interval are described below in conjunction with FIGS. 7 and 8.

In still other examples, the pacing escape interval 132 may be set based on RR intervals determined during the sensing without pacing mode 102, prior to the most recent R-wave sensed event before asystole detection. For example, intervals between consecutive R-waves 122 shown in FIG. 5A may be determined and used for setting the pacing escape interval 132. For example, pacing escape interval 132 may be set as an average of the RR intervals preceding asystole detection or a predetermined interval or percentage longer than the average of RR intervals preceding asystole detection.

Figure 6:
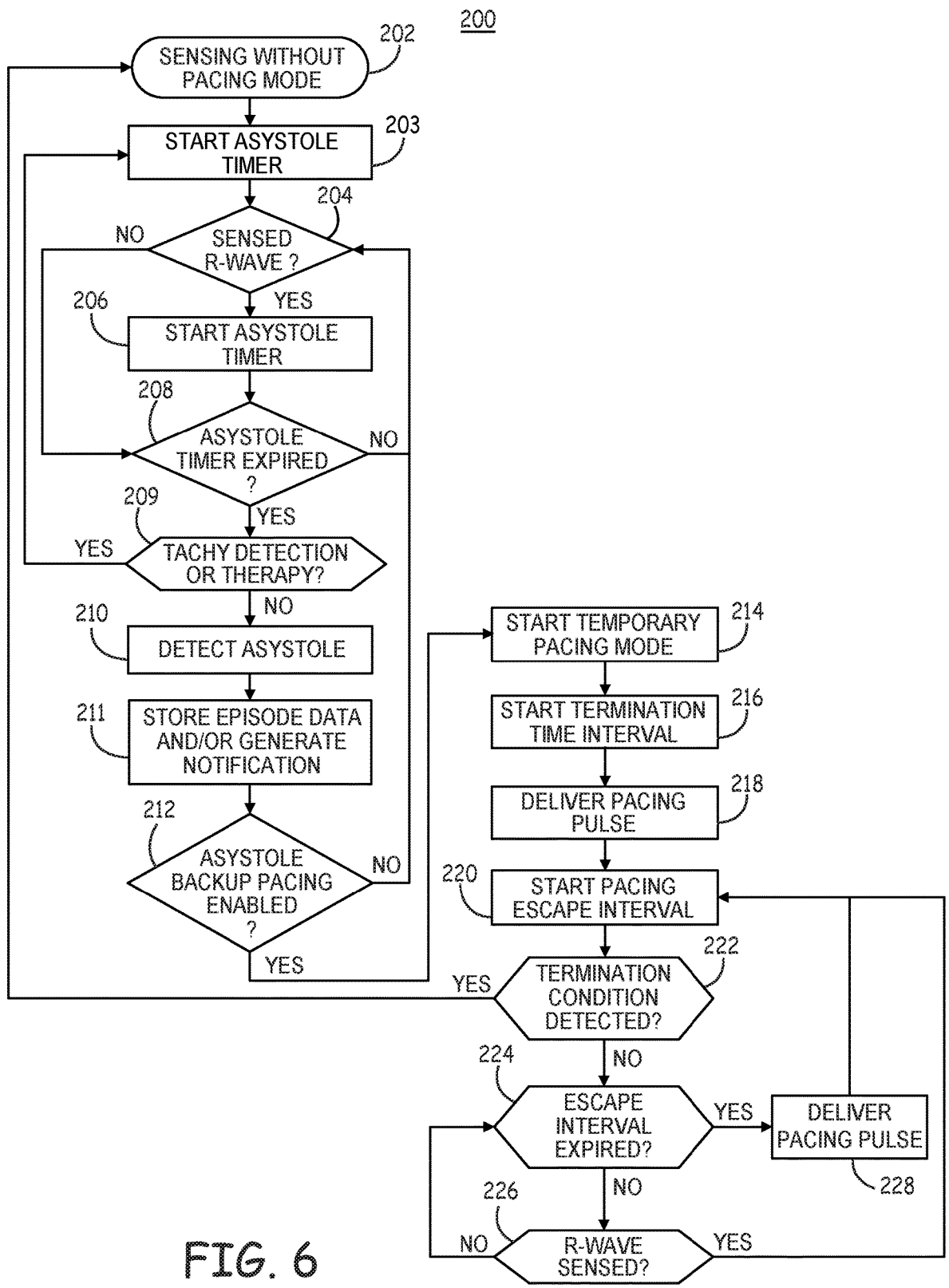
FIG. 6 is a flow chart of a method for controlling cardiac pacing by an ICD to provide backup pacing in response to detecting asystole.

FIG. 6 is a flow chart 200 of a method for controlling cardiac pacing by an ICD, such as the extra-cardiovascular ICD 14 of FIGS. 1A and 1B, to provide asystole backup pacing in response to detecting asystole. At block 202, the ICD is operating in the sensing without pacing mode. The sensing without pacing mode may be a programmable pacing mode or a default pacing mode of the ICD. The sensing without pacing mode may correspond to an OVO or ODO pacing mode in which no pacing pulses are delivered even when an RR interval is longer than a programmed asystole backup rate interval or a programmed bradycardia lower rate interval. The asystole backup rate interval used during a temporary pacing mode and the lower rate interval used during a permanent bradycardia pacing mode prevent the heart rate from going below a corresponding minimum rate, e.g., 30 beats per minute or 40 beats per minute, by delivering pacing pulses at the respective asystole backup rate or lower rate in the absence of sensed R-waves. During the sensing without pacing mode, pacing escape intervals are not set for scheduling a pacing pulse and a pacing pulse is not delivered even if the heart rate falls below the asystole backup rate or the lower rate programmed for use during a temporary or permanent pacing mode, respectively.

Upon enabling the sensing without pacing mode at block 202, an asystole timer is started at block 203. In the example described in FIG. 6, a single asystole timer is started that is used for both detecting asystole and for starting the recording of asystole episode data. However, as shown in FIG. 5 and described in further detail in FIG. 9, both a probable asystole time interval 124 and an asystole detection time interval 125 may be started. The probable asystole time interval may expire earlier than the asystole detection time interval and be used to control when recording of cardiac electrical signal episode data begins in anticipation of an asystole detection.

If an R-wave is sensed by the sensing circuit 86 at block 204, the asystole timer started at block 203 is restarted during the sensing without pacing mode as described in conjunction with FIG. 5. If the asystole timer has not expired, "No" branch of block 208, and another R-wave is sensed, "Yes" branch of block 204, the asystole timer is restarted at block 206. This process continues as long as the asystole timer does not expire. The ICD remains in the sensing without pacing mode.

If an R-wave is has not been sensed at block 204 before the asystole timer expires, "Yes" branch of block 208, the control circuit 80 detects asystole at block 210. Other asystole detection criteria may be required to be met in order to detect asystole at block 210. For example, if the asystole timer expires at block 208, control circuit 80 may verify at block 209 that a tachyarrhythmia episode is not being detected and that an anti-tachyarrhythmia therapy, which may include ATP or a shock therapy followed by post-shock pacing, is not being delivered before detecting the asystole at block 210. Asystole may be detected at block 210 during the sensing without pacing mode in response to an asystole detection threshold time interval expiring subsequent to a sensed R-wave when a tachyarrhythmia episode is not being detected and when a tachyarrhythmia therapy, e.g., ATP or a shock therapy and post-shock pacing, is not being delivered.

If a tachyarrhythmia detection is being made or an anti-tachyarrhythmia therapy is being delivered, "yes" branch of block 209, control circuit 80 may withhold switching to the temporary pacing mode by returning to block 203 to restart the asystole timer. It is to be understood that the check to determine if a tachyarrhythmia episode is being detected or an anti-tachyarrhythmia therapy is being delivered, as indicated at block 209, is not necessarily limited to a certain time point in the process of detecting asystole during the sensing without pacing mode. For example, a tachyarrhythmia detection may be made after detecting asystole at block 210 and an anti-tachyarrhythmia therapy may be scheduled or in process prior to switching to the sensing without pacing mode. In this case, control circuit 80 may withhold switching to the temporary pacing mode and controls the therapy delivery circuit 84 according to anti-tachyarrhythmia therapy control parameters, e.g., ATP therapy control parameters and/or shock therapy and post-shock pacing therapy control parameters.

It is recognized that ICD 14 may be configured to deliver post-shock pacing to aid the heart in recovering from a cardioversion/defibrillation shock, which can sometimes be followed by asystole. A tachyarrhythmia episode detection may still be in progress after shock delivery until normal sinus rhythm is detected. As such, a shock followed by asystole and post-shock pacing is considered to be within a tachyarrhythmia episode and under the control of a tachyarrhythmia mode of operation. In this situation, it is the shock pulse that is the leading event of the asystolic period, not an R-wave sensed outside of a tachyarrhythmia episode. Therapy delivery circuit 84 may deliver anti-tachyarrhythmia therapy utilizing low voltage and/or high voltage capacitors of therapy delivery circuit 84 such that capacitors and other output circuitry of therapy delivery circuit 84 are not controlled to operate in a temporary pacing mode of the bradycardia operating modes simultaneously with anti-tachyarrhythmia therapy delivery. The control circuit 80 may remain in the sensing without pacing mode of the bradycardia operating modes when a tachyarrhythmia episode or therapy is in progress, including during post-shock pacing.

In some examples, asystole episode data is stored in memory 82 at block 211. Asystole episode data may include a segment of the cardiac electrical signal including at least a portion of the asystole episode along with a time and date stamp. The segment of the cardiac electrical signal may include at least a portion of the asystole detection time interval preceding the asystole detection, a portion of the cardiac electrical signal prior to the sensed R-wave that started the asystole detection time interval, and/or a portion of the cardiac electrical signal after switching to a temporary asystole backup pacing mode as described below. Other data that may be stored may include an average heart rate prior to the asystole, the number of asystole detections over a predetermined period of time, e.g., one day, one week, one month, etc., patient activity data, and/or patient posture data. If the temporary pacing mode is a rate responsive mode, e.g., VVIR or VVTR, the patient activity data may be used in establishing a pacing escape interval meeting the patient's metabolic demand. Asystole episode data storage is not triggered in response to post-shock pacing associated with tachyarrhythmia therapy. Asystole episode data storage at block 211 is triggered by detection of asystole during the sensing without pacing mode, which withholds asystole detection during a post-shock period to allow the tachyarrhythmia operating mode to control therapy delivery.

In addition to or alternatively to storing asystole episode data at block 211, a patient and/or clinician notification may be generated at block 211 upon detecting asystole at block 210. A notification to the patient or clinician may be transmitted via telemetry circuit 88 to an external device. In some examples, a patient notification is generated by patient notification circuit 90, e.g., as an audible tone, vibration or muscle twitch stimulation. A patient and/or clinician notification may be generated only in response to the first asystole detection made since a most recent ICD interrogation and telemetry session with the external device 40. No further notifications are generated in response to subsequent asystole detections until another ICD interrogation session occurs. In other examples, a notification is generated only when the number of asystole detections reaches a threshold number or other notification criteria are met, such as a threshold number of pacing pulses delivered during one or more ventricular pacing mode time intervals started in response to detecting asystole. In some cases, a notification is generated each time asystole is detected. An asystole notification may be generated immediately following an asystole episode detection (or after a threshold number of asystole episodes are detected) and the notification may be immediately transmitted to an external device 40 or delivered to the patient or transmitted to external device 40 at a predetermined time of day.

In some examples, ICD 14 may be programmed to operate only in the sensing without pacing mode without automatic switching to a temporary pacing mode. For example, the physician may enable or disable the asystole backup pacing feature of the ICD while ICD 14 remains capable of detecting asystole episodes and storing asystole data. If asystole backup pacing is not enabled, "No" branch of block 212, the ICD 14 remains in the sensing without pacing mode and returns to block 204 to continue sensing R-waves and monitoring for asystole. No pacing is delivered, however, asystole episodes are detected and asystole episode data may be accumulated in memory for transmission to an external device 40 (shown in FIG. 1A) for display to a user for confirming the asystole detection(s) and managing patient therapies. As such, in some examples, ICD 14 is programmable in either a sensing without pacing mode with asystole backup pacing disabled or in a sensing without pacing mode with asystole backup pacing enabled.

When ICD 14 is programmed to operate in the sensing without pacing mode with asystole backup pacing enabled, control circuit 80 automatically switches to the temporary pacing mode at block 214 in response to the asystole detection made at block 210. In some examples, control circuit 80 starts a temporary pacing mode termination timer at block 216 to limit the time period that ICD 14 operates in the temporary pacing mode. In this way, the pacing mode may be referred to as a "temporary" mode in that after a predetermined time period or other termination condition is satisfied, the ICD 14 automatically switches from the temporary pacing mode back to the sensing without pacing mode.

Upon switching to the temporary pacing mode, the control circuit 80 enables the therapy delivery circuit 84 to start a pacing escape interval after which the first pacing pulse is delivered as shown in FIG. 5. In other examples, therapy delivery circuit 84 may be controlled to immediately deliver a pacing pulse at block 218, and start the pacing escape interval at block 220 after immediately delivery a pacing pulse. As described above in conjunction with FIG. 5, the pacing escape interval may be an asystole backup rate interval set to a minimum available pacing rate interval, to a bradycardia pacing lower rate interval, to a sensor-indicated rate interval for providing rate responsive pacing to meet the patient's metabolic demand, or an interval based upon one or more RR intervals occurring prior to the asystole detection.

At block 222, the control circuit 80 determines if a termination condition is detected. A termination condition may be detection of a tachyarrhythmia episode by control circuit 80, e.g., a VT or VF detection. If VT or VF is being detected and is programmed to be a termination condition, "Yes" branch of block 222, the control circuit 80 automatically switches back to the sensing without pacing mode (return to block 202). Another termination condition that may be detected at block 222 is the expiration of the temporary pacing mode termination timer started at block 216. When the termination timer expires, the temporary pacing mode is terminated, and the ICD automatically switches back to the sensing without pacing mode at block 202. The termination timer may be set to a predetermined time period, e.g., 30 seconds, one minute, two minutes, five minutes, 10 minutes or other predetermined time period.

In another example, a termination condition that may be detected at block 222 may be a threshold number of sensed R-waves, consecutive or non-consecutive. For example, if two to five R-waves (or another predetermined number) are sensed before the pacing mode termination timer expires, control circuit 80 may automatically switch back to the sensing without pacing mode to promote an intrinsic heart rhythm. As such, upon starting the termination time interval at block 216, an R-wave sensed event counter included in control circuit 80 may also be enabled. Consecutively sensed R-waves may be counted and if a pacing pulse is delivered the counter may be reset to zero. If a threshold number of consecutive R-waves, e.g., 3 to 5 R-waves, are sensed, the temporary pacing mode may be terminated early. In other examples the R-waves do not need to be sensed consecutively so that the R-wave sensed event counter is not reset to zero by a pacing pulse. In some instances, the counter is decremented in response to a delivered pacing pulse and incremented in response to a sensed R-wave. When the counter reaches a threshold value, the temporary pacing mode may be terminated.

In other examples, a user may manually terminate the temporary pacing mode by sending a command using external device 40 or by applying a magnet over ICD 14. If a magnet is detected by control circuit 80 or the command is received, the ICD 14 switches back to the sensing without pacing mode.

If no termination condition is detected at block 222, and the pacing escape interval started at block 220 has not expired, the control circuit 80 waits for the next sensed R-wave or expiration of the pacing escape interval, whichever comes first. If an R-wave is sensed at block 226, the pacing escape interval is restarted at block 220. The pacing pulse scheduled to be delivered at the expiration of the pacing escape interval is cancelled. The pacing escape interval may be reset to an asystole backup pacing interval, a bradycardia pacing lower rate interval, a rate responsive pacing interval, an interval based on RR intervals occurring prior to asystole detection, or to a hysteresis interval, as described above. It is understood that a blanking interval may be set following a pacing pulse during which sensing circuit 86 does not generate an R-wave sensed event signal, or any R-wave sensed event signals that are generated during the blanking interval are ignored by control circuit 80.

If a pacing escape interval expires, "Yes" branch of block 224, control circuit 80 controls therapy delivery circuit 84 to deliver a pacing pulse at block 228. The pacing pulse delivered at block 228 may be delivered by a high voltage output circuit or a low voltage output circuit according to any of the techniques described in conjunction with FIG. 4 and in the above-incorporated references. After a delivered pacing pulse, the pacing escape interval is restarted at block 220.

In some examples, a limited number of pacing pulses are delivered at the asystole backup rate interval, e.g., at an interval of 2 second resulting in 30 pulses per minute, and then the pacing escape interval is set to a hysteresis interval without requiring a sensed R-wave to start the hysteresis interval. For example, the pacing escape interval may be set to 2 seconds according to the preceding example upon each of a predetermined number of consecutive pacing pulses, e.g., five to thirty pacing pulses, then the control circuit 80 sets the pacing escape interval to a hysteresis pacing interval at block 220 that is longer than the asystole backup pacing interval, e.g., up to 3 seconds.

In still other examples, the first pacing pulse delivered at block 218 starts a pacing escape interval set to a hysteresis interval to allow intrinsic conduction to return after a single pacing pulse. If no R-wave is sensed, the next pacing pulse delivered at block 228 starts a pacing escape interval set to the asystole backup rate interval. The pacing escape interval may be set to the asystole backup rate interval for each pacing pulse delivered (or to the hysteresis interval if an R-wave is sensed or a predetermined number of pacing pulses have been delivered) until the termination time interval expires.

FIG. 7 is a timing diagram 300 of events during the temporary pacing mode started at block 214 of FIG. 6 according to one example. Pacing pulse 302 is delivered after switching to the temporary pacing mode, which may be after expiration of a first pacing escape time interval that was started immediately upon switching to the temporary pacing mode or immediately after switching to the temporary pacing mode. Control circuit 80 sets a pacing escape interval timer to a hysteresis interval 304 upon delivery of the first pacing pulse 302. A termination timer (not shown in FIG. 7) may also be started upon switching to the temporary pacing mode. The initial hysteresis interval 304 promotes intrinsic conduction over a paced rhythm. If the sensing circuit 86 does not sense an R-wave during the hysteresis interval 304, however, the second pacing pulse 306 is delivered. Upon delivering the second pacing pulse 306, control circuit 80 sets the pacing escape interval timer to an asystole backup pacing rate interval 308, which may be a minimum available rate interval, a programmed lower rate interval, or a sensor-indicated pacing rate interval if the temporary pacing mode is a rate responsive mode.

In some examples, all subsequent pacing pulses, e.g., pacing pulse 310, are delivered at the asystole backup rate interval 308 following an immediately preceding pacing pulse, e.g., pacing pulse 306, or a preceding R-wave sensed by the sensing circuit 86, until the termination timer expires or another temporary pacing mode termination condition is detected, whichever comes first. In other examples, if an R-wave sensed event signal 314 is produced by the sensing circuit 86 during an asystole backup rate interval 312, control circuit 80 sets the pacing escape interval timer to the hysteresis interval 316 to allow intrinsic conduction to occur. The hysteresis intervals 304 and 316 are longer than the asystole backup rate interval 308. Hysteresis intervals 304 and 316 are shown to be equal but the initial hysteresis interval 304 may be different than the hysteresis interval 316 set in response to R-wave sensed event signal Rs 314. The pacing pulse scheduled to occur at the expiration of the asystole backup rate interval 312 is withheld. If the hysteresis interval 316 expires without an R-wave sensed by sensing circuit 86, a pacing pulse 318 is delivered. The pacing escape interval timer may be reset to the asystole backup rate interval upon delivery of pacing pulse 318. If another R-wave is sensed during hysteresis interval 316, the pacing escape interval timer is reset to the hysteresis interval.

FIG. 8 is another timing diagram 400 of events during a temporary pacing mode started in response to detecting asystole during the sensing without pacing mode according to another example. In this example, the pacing escape interval timer is set to a first pacing escape interval 404 upon switching to the temporary pacing mode at 402. The first pacing pulse 405 is delivered upon expiration of the first pacing escape interval 404. Pacing interval 404 may be a shorter interval than an asystole backup pacing rate interval 408 to provide an initial pacing rate faster than the programmed asystole backup pacing rate. An initially faster rate may provide hemodynamic support needed after a long asystolic interval. While a single pacing pulse 405 is shown delivered at the initial rate interval 404, a series of two or more pacing pulses may be delivered at the initial pacing escape interval 404. For example, a predetermined number such as 2, 3, 5 or other predetermined number of pacing pulses may be delivered at the initial rate interval 404. The initial rate interval 404 may be 50 to 1000 ms shorter than the programmed asystole backup pacing rate interval 408. In one instance, if the asystole backup pacing rate interval is two seconds, to provide a backup asystole pacing rate of 30 pulses per minute, the initial pacing rate interval 404 may be one second to provide one or more heart beats at a rate of 60 beats per minute. In other examples, the first pacing escape interval 404 may be determined by control circuit 80 as a sensor-indicated pacing rate based on a patient activity signal received from sensor 92.

After a predetermined number of pacing pulses 405 delivered at the initial pacing escape interval 404, one or more subsequent pacing pulses 406, 407, and 410 are scheduled and delivered at the asystole backup interval 408 (in the absence of R-wave sensed event signals from sensing circuit 86). Control circuit 80 may include a counter for counting the pacing pulses 405, 406, 407 and 410 delivered during the temporary pacing mode. In some examples, all delivered pacing pulses are counted by incrementing the counter each time a pacing pulse is delivered. In other examples, the counter is reset to zero or decremented when an R-wave is sensed by sensing circuit 86.

Control circuit 80 compares the counter to a predetermined number of pacing pulses. If the predetermined number of pacing pulses is reached, the pacing escape interval timer is set to a hysteresis interval 412 longer than the asystole backup rate interval 408 upon delivering the last pacing pulse 410 of the predetermined number of pacing pulses. By setting a hysteresis interval 412 periodically during the pacing mode, intrinsic conduction may be allowed to return to minimize pacing. If the sensing circuit 86 does not sense an R-wave during the hysteresis interval 412, a pacing pulse 414 is delivered, and the control circuit 80 may return to setting the pacing escape interval timer to the asystole backup rate interval 408 for another predetermined number of pacing pulses (or until a termination condition is detected).

A total number of pacing pulses delivered during the temporary pacing mode may be counted by control circuit 80 and included in asystole episode data stored in memory 82 along with a cardiac electrical signal segment. A histogram of pacing intervals, e.g., intervals 304, 308, 312, and 316 in FIG. 7 or intervals 404, 408 and 412 in FIG. 8, occurring during the temporary pacing mode may also be stored with the asystole episode data for transmission to external device 40.

Figure 9:
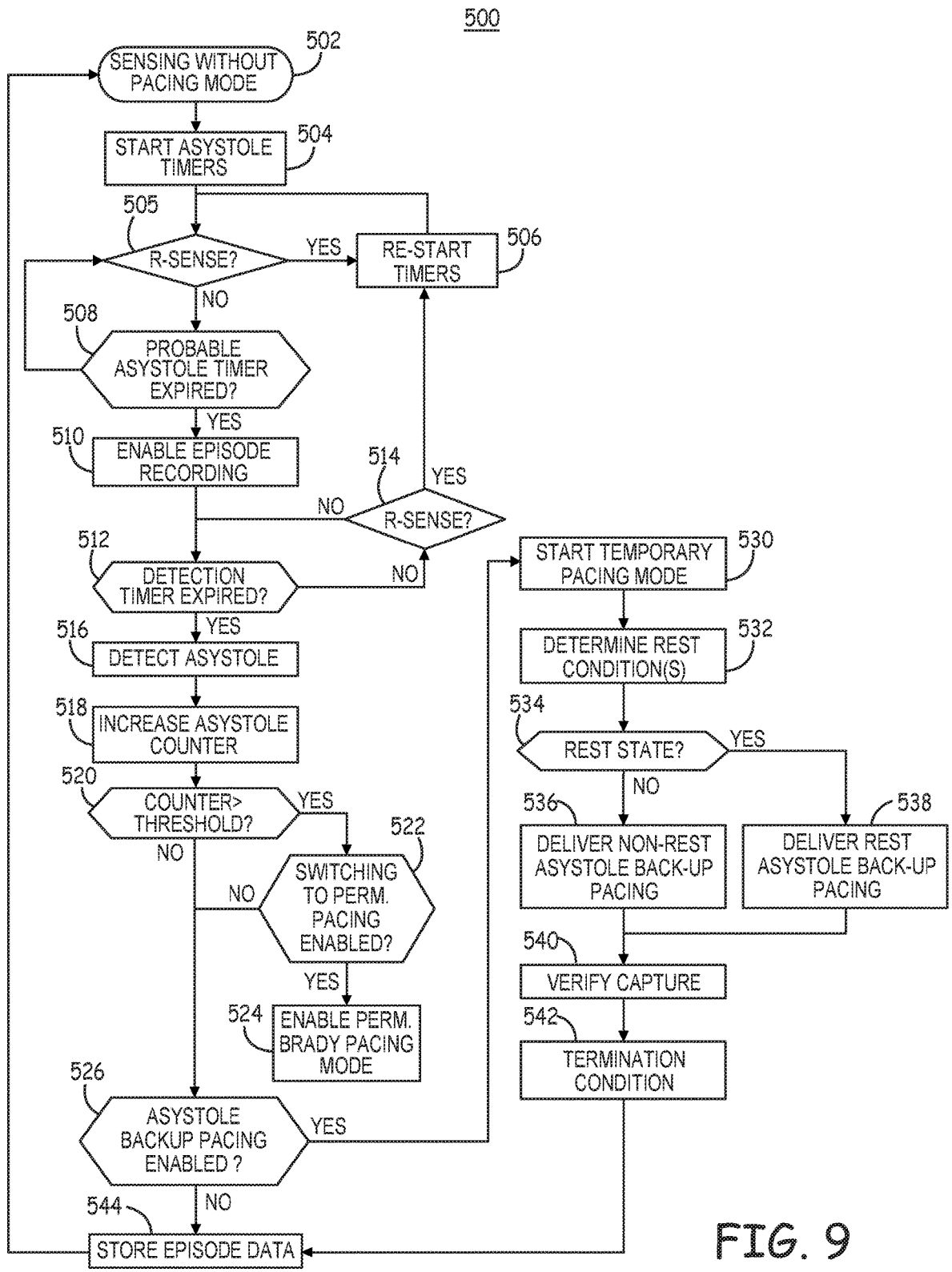
FIG. 9 is a flow chart of a method for controlling a response to detecting asystole by an ICD according to another example.

FIG. 9 is a flow chart 500 of a method for controlling a response to detecting asystole by ICD 14 according to another example. At block 502, the ICD is operating in the sensing without pacing mode. Upon initiating the sensing without pacing mode, control circuit 80 starts asystole timers, which may include a probable asystole timer and an asystole detection timer as shown in FIG. 5. If control circuit 80 receives an R-wave sensed event signal (block 505), the asystole timers are restarted at block 506. If the probable asystole timer expires at block 508, control circuit 80 enables recording of a cardiac signal episode in memory 82 at block 510. As described in conjunction with FIG. 5, a probable asystole timer may be set to a shorter time interval than the asystole detection timer so that a recording of the cardiac electrical signal may be obtained leading up to asystole detection and prior to starting asystole backup pacing.

If the asystole detection timer has not expired (block 512) and an R-wave sensed event signal is received by control circuit 80, "yes" branch of block 514, the asystole timers are restarted at block 506. In some examples, if the probable asystole timer expires but the asystole detection timer does not, the episode recording started at block 520 may be terminated and may be cleared from memory 82 or overwritten the next time the probable asystole timer expires. If the asystole detection timer does expire before an R-wave sensed event signal is received, "yes" branch of block 512, control circuit 80 detects asystole at block 516. Although in the example described in FIG. 9 two separate timers are utilized, a probable asystole timer and an asystole detection timer, only a single timer may be utilized as described in blocks 202, 203, 204, 206, and 208 of FIG. 6 in place of the two timer technique described above.

In some examples, an asystole detection counter may be increased at block 518 in response to detecting the asystole. The asystole detection counter may be increased each time an asystole is detected and may be reset upon an interrogation command, upon user command or upon switching from a permanent bradycardia pacing mode to the sensing without pacing mode. At block 520, the asystole counter is compared to a threshold for switching from the sensing without pacing mode to a permanent bradycardia pacing mode.

If the counter has not reached the threshold for switching to a permanent bradycardia pacing mode at block 520, and asystole backup pacing is not enabled, "no" branch of block 526, the control circuit 80 stores the asystole episode data at block 544 and continues to monitor for asystole episodes in the sensing without pacing mode by returning to block 502. Asystole episodes may continue to be detected during the sensing without pacing mode for the useful purpose of collecting and storing cardiac electrical signal data of the asystole episode(s) (enabled at block 510) for transmission to an external device 40 for review by a physician. Asystole episode data recorded at block 544 may include a cardiac electrical signal segment, RR interval data preceding the asystole detection, patient activity data, patient posture data, or other data, e.g., as described in conjunction with block 211 of FIG. 6. The asystole episode data obtained and recorded by ICD 14 in the ambulatory patient provides useful information to a clinician for making diagnostic and therapy management decisions. Such recordings of spontaneous asystole episodes may not be obtainable in a clinic or office visit setting or, if obtained, may represent different clinical conditions that are not necessarily representative of spontaneous asystolic events occurring outside a clinical setting.

If the counter has reached a threshold number of asystole detections at block 520, the ICD 14 may automatically switch to a permanent bradycardia pacing mode at block 524 depending on whether switching to permanent bradycardia pacing is enabled or disabled. ICD 14 may be programmably enabled to operate in the sensing without pacing mode only, with both automatic switching to a temporary pacing mode for asystole backup pacing support disabled and automatic switching to a permanent bradycardia pacing mode disabled. In other cases, the ICD 14 may be programmed to operate in the sensing without pacing mode with automatic switching to the temporary, asystole backup pacing mode enabled but with automatic switching to a permanent bradycardia pacing mode disabled. In still other cases, ICD 14 may be programmed to operate in the sensing without pacing mode with both automatic switching to a temporary pacing mode enabled and automatic switching to a permanent bradycardia pacing mode enabled.

Depending on the pacing capture threshold required for pacing the patient's heart using extra-cardiovascular electrodes, and the patient's tolerance for extra-cardiovascular pacing, a clinician may or may not enable ICD 14 to automatically switch to a permanent bradycardia pacing mode. In some cases, skeletal muscle stimulation or other unintended stimulation caused by the extra-cardiovascular pacing may be poorly tolerated or painful to a patient. Accordingly, multiple programmable bradycardia therapy operating mode options may be available including sensing without pacing only; sensing without pacing and automatic switching to temporary asystole backup pacing enabled; sensing without pacing with automatic switching to temporary asystole backup pacing disabled and automatic switching to permanent bradycardia pacing enabled; and sensing without pacing with both automatic switching to temporary asystole backup pacing and automatic switching to permanent bradycardia pacing enabled. As used herein, a temporary pacing mode refers to a pacing mode that switches back to the sensing without pacing mode after a termination condition is detected as described previously herein. A "permanent pacing mode" refers to a pacing mode that remains in effect until the pacing mode is reprogrammed by a user, e.g., using external device 40, without automatic switching back to the sensing without pacing mode. In some cases, however, a permanent pacing mode may be automatically switched back to the sensing without pacing mode to conserve longevity of power source 98 if a pacing pulse has not been delivered for a predetermined time period, e.g., for 24 hours, three days, one week or other predetermined time period.

If the asystole detection counter reaches the threshold at block 520, and automatic switching to permanent bradycardia pacing is enabled, as determined at block 522, ICD 14 automatically switches to a permanent bradycardia pacing mode at block 524. During the permanent bradycardia pacing mode, bradycardia pacing is delivered according to a programmed lower pacing rate and bradycardia pacing mode, such as VVI, VVI(R), VVT or VVT(R) and other pacing control parameters. The pacing lower rate may be adjusted to a sensor-indicated pacing rate when rate-responsive pacing is enabled, such as activity sensor based, rate-responsive pacing.

If the counter has not reached the threshold at block 520, or if it has and automatic switching to a permanent bradycardia pacing mode is not enabled but asystole backup pacing is enabled, "yes" branch of block 526, the control circuit 80 starts the temporary asystole backup pacing mode at block 530. In some examples, control circuit 80 may determine one or more rest conditions at block 532 upon switching to the temporary asystole backup pacing mode. A rest condition may be any of the time of day, patient activity and/or patient posture determined at block 532. Patient activity and/or patient posture may be determined by control circuit 80 based on a signal received from the activity and posture sensor 92. Control circuit 80 may include a clock or 24-hour timer initialized to a real time setting for determining time of day. The rest condition(s) may be determined from signals received by control circuit 80 from activity/posture sensor 92 prior to the asystole detection and prior to the onset of the asystole episode, e.g., from activity and posture signals obtained over a time interval prior to the R-wave that starts the asystole episode.

At block 534, control circuit 80 determines whether the patient is in a resting state based on whether or not one or more rest conditions are satisfied. For example, if activity and/or posture is/are determined at block 532, one rest condition may be a low level of activity and another rest condition may be a non-upright posture. Another rest condition may be time of day. If the time of day is nighttime or a programmable time period that the patient is known to typically be resting, a rest state is detected at block 534. A rest state may be detected based solely on time of day based on a clock signal included in control circuit 80 or any combination of patient activity, patient posture, and/or time of day. If a rest state is detected, the asystole backup pacing is controlled according to programmed resting state asystole backup pacing control parameters at block 538.

A first set of control parameters may be stored in memory 82 for controlling the temporary asystole backup pacing mode during a detected rest state, and a second set of control parameters may be stored for controlling the temporary asystole backup pacing mode when a rest state is not detected. Some patients may experience long ventricular pauses or very slow ventricular rates during a resting state, for example at night while the patient is asleep. Since an extra-cardiovascular pacing pulse that successfully captures the heart may also capture skeletal muscle or other non-cardiac tissue in some patients, the patient may perceive the pacing pulse, which could disrupt sleep. Accordingly, in some cases, resting state control parameters may include a longer asystole backup rate interval for controlling the pacing escape interval than the non-resting state control parameters. A resting state asystole backup pacing rate interval may be greater than or equal to two seconds, three seconds, four seconds or more and a non-resting state asystole backup pacing rate interval may be between one and two seconds, for example. In other examples, asystole backup pacing may be withheld during the resting state so that no extra-cardiovascular pacing pulses are delivered during the temporary pacing mode when a resting state is detected based on one or more rest conditions.

In still other examples, other pacing control parameters may be set differently for controlling asystole backup pacing during a detected resting state than during a non-resting state. For example a lower pulse voltage amplitude, a lower pulse voltage amplitude and longer pulse width, or a lower pacing pulse amplitude safety margin or pulse width safety margin may be used to reduce the likelihood of sleep disturbance during the resting state due to extra-cardiac stimulation. In one instance, the pacing pulse amplitude is set to zero when a resting state is detected.

Other control parameters that may be different during the resting state than during a non-resting state may relate to the duration and number of pulses being delivered. For example, a shorter termination time interval may be applied to terminate the temporary asystole backup pacing mode earlier during rest than during non-rest. Other termination conditions, such as a maximum number of pacing pulses may be reduced to reduce the total number of pulses delivered. The number of pulses delivered at the asystole backup pacing rate interval before a hysteresis interval (e.g., interval 412 in FIG. 8) is scheduled may be reduced in order to allow an earlier return to intrinsic rhythm and/or a longer hysteresis interval may be used after a threshold number of pulses is delivered as shown in FIG. 8 or after sensing an R-wave as shown in FIG. 7.

The non-resting state asystole backup pacing control parameters may include an initial, first pacing escape interval for controlling delivery of one or more pulses at an initial, accelerated rate, such as the first pacing escape interval 404 that is shorter than the asystole backup pacing rate interval 408 as shown in FIG. 8. This feature of an initial shorter pacing escape interval may be disabled during resting state asystole backup pacing. In general, the resting state control parameters may be set to less intensive settings to reduce the energy, number and/or rate of pacing pulses delivered during the temporary asystole backup pacing mode when a resting state is detected.

The resting state asystole backup pacing is delivered at block 538 according to programmed resting state control parameters. If a resting state is not detected at block 534, the asystole backup pacing is delivered at block 536 according to the non-resting state asystole backup pacing control parameters.

During the temporary asystole backup pacing mode, including both non-resting state asystole backup pacing delivered at block 536 and resting state asystole backup pacing if delivered at block 538, the control circuit 80 may verify capture at block 540. Capture of one or more delivered pacing pulses may be verified, for example, based on receiving an R-wave sensed event signal from sensing circuit 86 within a capture verification time interval following delivery of a pacing pulse. In some cases, if capture is not initially verified, the pacing output, either the pacing pulse voltage amplitude and/or the pacing pulse width, may be increased until capture is verified at block 540.

When a termination condition is detected at block 542, asystole episode data is stored at block 544 along with the cardiac electrical signal recording that was enabled at block 510. The asystole episode data may include data relating to patient activity, patient posture, time of day, rest conditions used to detect a resting state, whether or not a resting state was detected, pacing pulse amplitude and/or width, capture verification data that may include the pacing pulse amplitude and/or pulse width at which capture was verified, number of pulses delivered, number of pulses delivered at respective pacing pulse intervals, the termination condition detected, the duration of the temporary asystole backup pacing mode, the duration of the asystole episode, and RR interval data leading up to the asystole episode. After termination of the temporary asystole backup pacing mode, control circuit 80 returns to the sensing without pacing mode at block 502.

Figure 10:
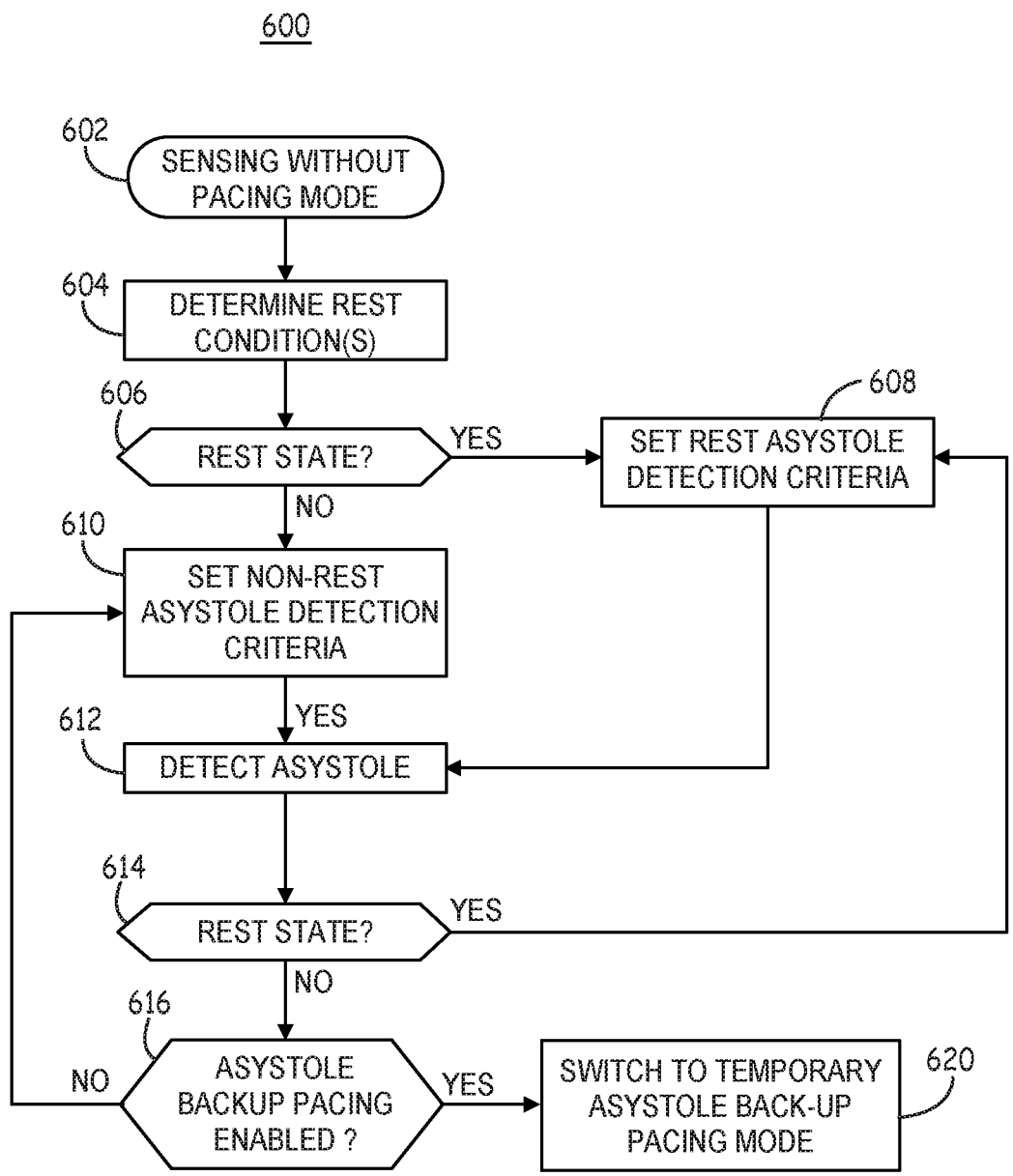
FIG. 10 is a flow chart of a method for controlling automatic switching to a temporary asystole backup pacing mode by an ICD according to yet another example.

FIG. 10 is a flow chart 600 of a method for controlling automatic switching to a temporary asystole backup pacing mode by ICD 14 according to another example. While the flow chart 500 of FIG. 9 shows detection of a resting state being performed after switching to the temporary asystole backup pacing mode, it is to be understood that operations represented by the flow chart 500 and other flow charts presented herein may be performed in a different order or combination than the specific order and combination shown by the illustrative examples. For instance, if asystole backup pacing is to be entirely withheld during a detected resting state, operations performed at blocks 532 and 534 for determining rest conditions and detecting a resting state may be determined during the sensing without pacing mode for withholding automatic switching to the temporary asystole backup pacing mode.

As shown in FIG. 10, during the sensing without pacing mode in effect at block 602, the rest condition(s) may be determined at block 604 prior to starting asystole timer(s) or detecting asystole. Control circuit 80 may set asystole detection criteria to a first set of criteria at block 608 when a resting state is detected ("yes" branch of block 606) and to a second set of asystole detection criteria at block 610 when a resting state is not detected ("no" branch of block 606). For example, the asystole detection timer may be to a first asystole detection time interval during a detected resting state and to a second asystole detection time interval when a resting state is not detected. The first asystole detection time interval may be a relatively longer time interval, e.g., at least four seconds or longer, and the second asystole detection timer interval may be relatively shorter than the first asystole detection time interval, e.g., at least two seconds but less than the first asystole detection time interval.

In this way asystole detection during a detected resting state may require a longer ventricular pause to detect asystole than during a non-resting state. A relatively longer ventricular pause may be tolerated by the patient during rest without requiring asystole backup pacing. During a non-resting state, however, a relatively longer ventricular pause may lead to hemodynamic insufficiency or physical symptoms justifying a relatively shorter asystole detection time interval during a non-resting state than during a resting state.

If a probable asystole timer is set, as described in conjunction with FIG. 9, the probable asystole timer may be set to the same time interval at blocks 608 and 610 so that triggering of cardiac electrical signal storage occurs after the same time interval during both resting and non-resting states. In other examples, the probable asystole timer may be set to a longer time interval during the resting state than during the non-resting state.

At block 612, asystole is detected according to one of the detection criteria set at either block 608 or 610. At block 614, control circuit 80 may determine whether a resting state was detected at block 606 or determine whether a resting state is now detected based on different rest condition criteria than the criteria used at block 606. For instance, a resting state may be detected at block 606 based only on time of day such that different asystole detection criteria are used at night than during the day. Detection of a resting state at block 614, however, may additionally or alternatively require the patient activity and/or patient posture meet a rest condition in order to detect a resting state. If a resting state is detected based on one or more determined rest conditions at block 614, or based on the prior detection of a resting state made at block 606, control circuit 80 may withhold automatic switching to the temporary asystole backup pacing mode by returning to block 608. The automatic switching to the temporary asystole backup pacing mode at block 530 may be withheld to prevent asystole backup pacing while the patient is determined to be in a resting state. ICD 14 remains in the sensing without pacing mode, until an asystole detection is made and a resting state is not detected.

If a resting state is not detected at block 614, and asystole backup pacing is enabled at block 616, control circuit 80 automatically switches to the temporary asystole backup pacing mode at block 620. If asystole backup pacing is not enabled, "no" branch of block 616, the control circuit 80 remains in the sensing without pacing mode and returns to block 610 to continue utilizing the non-rest asystole detection criteria based on the resting state not being detected at block 614. In other examples, if a different set of resting state asystole detection criteria is used at block 606 than at block 614, the control circuit 80 may return to block 606 for determining if a resting state exists according to a first set of resting state detection criteria after block 614 ("yes" branch) and after block 616 ("no" branch). A first set of resting state detection criteria used at block 606, e.g., time of day only, may be different than a second set of resting state detection criteria used at block 614, e.g., patient activity and/or patient posture in addition to or alternatively to time of day. These different sets of resting state detection criteria allow automatic switching to the temporary asystole backup pacing mode in the event of asystole detection occurring at night according to resting state asystole detection criteria, when the patient is typically at rest, but the patient happens to be upright and/or active and the need for asystole backup pacing is properly indicated.

Figure 11:
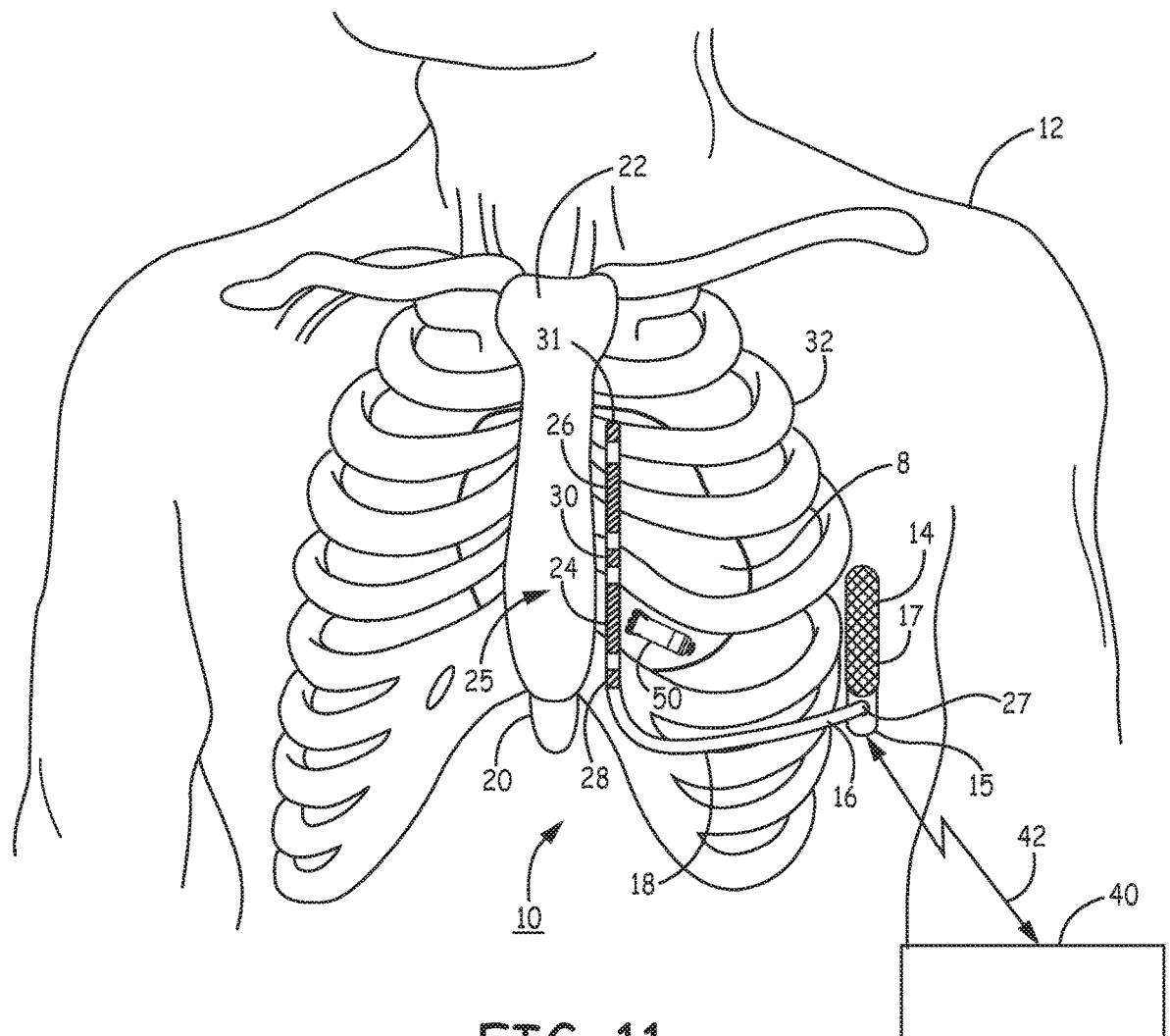
FIG. 11 is a conceptual diagram of an ICD system that may perform asystole detection and provide an asystole response according to another example.

FIG. 11 is a conceptual diagram of an ICD system that may perform asystole detection and provide an asystole response according to another example. Techniques disclosed herein have been described in conjunction with an ICD system including an implantable medical lead carrying extra-cardiovascular electrodes, but aspects of these techniques may be utilized in conjunction with other cardiac electrical sensing lead and electrode systems. For example, the techniques for detecting asystole and providing a response to detecting the asystole as described in conjunction with the accompanying drawings may be implemented in any implantable or external medical device enabled for sensing cardiac electrical signals, including implantable pacemakers, ICDs or cardiac monitors coupled to transvenous or epicardial leads carrying sensing electrodes; leadless pacemakers, ICDS or cardiac monitors having housing-based sensing electrodes; and external pacemakers, defibrillators, or cardiac monitors coupled to external, surface or skin electrodes.

For example, system 10' shown in FIG. 11 may include ICD 14 coupled to extra-cardiovascular lead 16 as described in conjunction with FIGS. 1A-2C above and may further include an intra-cardiac pacemaker 50. Examples of ICD systems including an intracardiac pacemaker or pacing pulse delivery device and an ICD coupled to an extra-cardiovascular lead are generally disclosed in U.S. Pat. No. 9,168,380 (Greenhut, et al.) and in U.S. patent application Ser. No. 14/823,405 (Sharma, et al.). These systems including an intracardiac pulse delivery device may be configured to perform the techniques disclosed herein for detecting asystole and providing an asystole response, which may include storing asystole episode data, switching from a sensing without pacing mode to a temporary backup pacing mode and/or switching to a permanent bradycardia pacing mode. Detection of asystole may be performed by the ICD 14 and/or by the intracardiac pacemaker 50 in the example system 10'. Intracardiac pacemaker 50 may perform the automatic switching to the temporary or permanent pacing mode automatically or in response to a signal from ICD 14 for delivering the asystole backup pacing, e.g., as described in conjunction with FIGS. 5A, 5B, 7 and 8.

Thus, a method and apparatus for detecting and responding to asystole in an ICD have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. An implantable cardioverter defibrillator (ICD) system, comprising:
   a sensing circuit configured to receive a cardiac electrical signal via a sensing electrode vector and sense cardiac events from the cardiac electrical signal;
   a therapy delivery circuit configured to deliver electrical pacing pulses to a heart of a patient via a pacing electrode vector; and
   a control circuit coupled to the sensing circuit and the therapy delivery circuit and configured to automatically switch between a sensing without bradycardia pacing mode and a temporary bradycardia pacing mode, and further configured to:

detect asystole based on the cardiac electrical signal without delivering a pacing pulse in response to detecting the asystole while operating in the sensing without pacing mode, and switch from the sensing without bradycardia pacing mode to the temporary bradycardia pacing mode only in response to detecting the asystole.

2. The ICD system of claim 1, wherein the control circuit is configured to start a pacing escape interval upon switching to the temporary bradycardia pacing mode without delivering a pacing pulse until the pacing escape interval expires without sensing an R-wave by the sensing circuit during the pacing escape interval.

3. The ICD system of claim 1, further comprising:
a memory coupled to the control circuit; and
a telemetry circuit configured for bi-directional wireless communication with an external device,
wherein the control circuit is configured to
store a segment of the cardiac electrical signal in the memory in response to detecting the asystole, and
control the telemetry circuit to transmit the stored cardiac electrical signal segment to the external device.

4. The ICD system of claim 1, further comprising a memory coupled to the control circuit,
wherein the control circuit is configured to:
set a first asystole time interval in response to an R-wave sensed by the sensing circuit;
set a second asystole time interval in response to the sensed R-wave;
enable recording of a segment of the cardiac electrical signal in the memory in response to the first asystole time interval expiring without sensing a next R-wave by the sensing circuit during the first asystole time interval; and
detect the asystole in response to the second asystole time interval expiring without sensing a next R-wave by the sensing circuit during the second asystole time interval.

5. The ICD system of claim 4, wherein the first time interval is shorter than the second time interval.

6. The ICD system of claim 1, wherein the control circuit is configured to:
detect a termination condition; and
switch from the temporary bradycardia pacing mode back to the sensing without bradycardia pacing mode upon detection of the termination condition.

7. The ICD system of claim 6, wherein:
the ICD further includes a telemetry circuit configured for bi-directional wireless communication with an external device; and
the control circuit is configured to detect the termination condition by detecting one of:
an expiration of a predetermined termination time interval;
a tachyarrhythmia episode;
a magnet applied over the ICD,
receipt of a termination command by the telemetry circuit,
a predetermined number of pacing pulses delivered during the temporary bradycardia pacing mode, or
a predetermined number of sensed R-waves during the temporary bradycardia pacing mode.

8. The ICD system of claim 1, wherein the control circuit is configured to control the therapy delivery circuit to:
set a pacing escape interval to a first value upon switching to the temporary bradycardia pacing mode;
deliver up to a predetermined number of pacing pulses at a rate corresponding to the first value when an R-wave is not sensed by the sensing circuit during the pacing escape interval set to the first value;
set the pacing escape interval to a second value longer than the first value after a last one of the predetermined number of pacing pulses is delivered at the rate corresponding to the first value; and
deliver a subsequent pacing pulse at a rate corresponding to the second value when an R-wave is not sensed during the pacing escape interval set to the second value.

9. The ICD system of claim 1, wherein the control circuit is configured to control the therapy delivery circuit to:
set a pacing escape interval to a first value upon switching to the temporary bradycardia pacing mode;
deliver up to a first predetermined number of first pacing pulses at a first rate corresponding to the first value of the pacing escape interval when an R-wave is not sensed by the sensing circuit during the pacing escape interval set to the first value;
set the pacing escape interval to a second value longer than the first value after the first predetermined number of pacing pulses are delivered at the first rate;
deliver up to a second predetermined number of second pacing pulses at a second rate corresponding to the second value of the pacing escape interval when an R-wave is not sensed during the pacing escape interval set to the second value;
set the pacing escape interval to a third value that is longer than the second value upon delivering a last one of the second predetermined number of second pacing pulses;
in response to the pacing escape interval set to the third value expiring without an R-wave sensed by the sensing circuit, deliver a third pacing pulse upon expiration of the pacing escape interval set to the third value; and
set the pacing escape interval to the second value in response to delivering the third pacing pulse.

10. The ICD system of claim 1, wherein the control circuit is configured to:
determine at least one rest condition;
determine whether the patient is in one of a rest state or a non-rest state based on the at least one rest condition;
in response to determining the patient being in the rest state, control the therapy delivery circuit to deliver asystole backup pacing during the temporary bradycardia pacing mode according to a first setting of a pacing control parameter; and
in response to determining the patient is in the non-rest state, control the therapy delivery circuit to deliver asystole backup pacing during the temporary bradycardia pacing mode according to a second setting of the pacing control parameter different than the first setting.

11. The ICD system of claim 10, wherein the ICD further comprises a sensor producing a signal correlated to at least one of patient activity or patient posture;
the control circuit being configured to determine the at least one rest condition by determining at least one of a time of day, a patient activity, or a patient posture.

12. The ICD system of claim 10, wherein the pacing control parameter is one of a pacing escape interval, a predetermined number of pacing pulses, a pacing pulse amplitude, a hysteresis interval, or a temporary bradycardia pacing mode termination condition.

13. The ICD system of claim 1, wherein the control circuit is configured to:
detect a rest state of the patient during the sensing without bradycardia pacing mode; and in response to detecting the rest state, perform at least one of:
    set an asystole detection timer to a first time interval that is longer than a second asystole detection timer used to detect asystole when a rest state is not detected; or
    withhold switching to the temporary bradycardia pacing mode.

14. The ICD system of claim 1, wherein the control circuit is configured to:
    increase an asystole episode counter in response to detecting the asystole;
    compare the asystole episode counter to a permanent pacing mode switch threshold;
    in response to the permanent pacing mode switch threshold being reached, determine if switching to a permanent pacing mode is enabled;
    switch from the sensing without bradycardia pacing mode to the permanent pacing mode in response to switching to the permanent pacing mode being enabled; and
    control the therapy delivery circuit to deliver cardiac pacing according to the permanent pacing mode.

15. The ICD system of claim 1, further comprising at least one of:
    a patient notification circuit configured to generate a notification signal perceivable by the patient; or
    a telemetry circuit configured to transmit a notification signal to an external device,
    wherein the control circuit is configured to control at least one of the patient notification circuit or the telemetry circuit to generate a notification in response to detecting the asystole.

16. The ICD system of claim 1, further comprising an extra-cardiovascular lead configured to be coupled to the ICD, the extra-cardiovascular lead carrying at least one electrode of the extra-cardiovascular pacing electrode vector.

17. The ICD system of claim 1, wherein the control circuit is further configured to:
    trigger the therapy delivery circuit to deliver a pacing pulse in response to a cardiac event being sensed by the sensing circuit after switching to the temporary bradycardia pacing mode, the pacing pulse being delivered by the therapy delivery circuit within a physiological refractory period of the sensed cardiac event.

18. The ICD system of claim 1, wherein the control circuit is further configured to:
    deliver a pacing pulse upon switching to the temporary bradycardia pacing mode; and
    start a pacing escape interval in response to delivering the pacing pulse.

19. The ICD system of claim 1, wherein the control circuit is configured to detect the asystole by:
    starting an asystole timer;
    determining that the asystole timer expires without an R-wave being sensed by the sensing circuit since starting the asystole timer; and
    detect the asystole in response to the asystole timer expiring without an R-wave being sensed.

20. The ICD system of claim 19, wherein the control circuit is configured to determine that the asystole timer expires by determining that the asystole timer expires after at least two seconds without an R-wave being sensed by the sensing circuit since starting the asystole timer.

21. A method, comprising:
    receiving a cardiac electrical signal;
    operating in a sensing without bradycardia pacing mode;
    detecting asystole based on the cardiac electrical signal without delivering a pacing pulse in response to detecting the asystole while operating in the sensing without bradycardia pacing mode; and
    switching from the sensing without bradycardia pacing mode to a temporary bradycardia pacing mode only in response to detecting the asystole.

22. A non-transitory, computer readable medium storing instructions which, when executed by a control circuit of an implantable medical device, cause the device to:
    receive a cardiac electrical signal;
    operate in a sensing without bradycardia pacing mode;
    detect asystole based on the cardiac electrical signal without delivering a pacing pulse in response to detecting the asystole while operating in the sensing without bradycardia pacing mode; and
    switch from the sensing without bradycardia pacing mode to a temporary bradycardia pacing mode only in response to detecting the asystole.

* * * * *